US009612250B2

(12) United States Patent
Perello Bestard et al.

(10) Patent No.: US 9,612,250 B2
(45) Date of Patent: Apr. 4, 2017

(54) METHOD FOR THE DIRECT DETECTION AND/OR QUANTIFICATION OF AT LEAST ONE COMPOUND WITH A MOLECULAR WEIGHT OF AT LEAST 200

(71) Applicant: Laboratorios Sanifit, S.L., Palma (ES)

(72) Inventors: Joan Perello Bestard, Palma de Mallorca (ES); Ciriaco Maraschiello de Zuani, Barcelona (ES); Irene Lentheric, Barcelona (ES); Paula Mendoza de las Heras, Barcelona (ES); Fernando Tur Espinosa, Palma de Mallorca (ES); Eva Tur Tur, Palma de Mallorca (ES); Maximo Encabo Alarcon, Barcelona (ES); Eva Martin Becerra, Palma de Mallorca (ES); Maria de Mar Benito Amengual, Palma de Mallorca (ES); Bernat Isern Amengual, Palma de Mallorca (ES)

(73) Assignee: Laboratorios Sanifit, S.L., Palma (ES)

( * ) Notice: Subject to any disclaimer, the term of this patent is extended or adjusted under 35 U.S.C. 154(b) by 0 days.

(21) Appl. No.: 14/350,265

(22) PCT Filed: Oct. 8, 2012

(86) PCT No.: PCT/EP2012/069878
§ 371 (c)(1),
(2) Date: Apr. 7, 2014

(87) PCT Pub. No.: WO2013/050603
PCT Pub. Date: Apr. 11, 2013

(65) Prior Publication Data
US 2015/0212101 A1    Jul. 30, 2015

(30) Foreign Application Priority Data
Oct. 6, 2011 (EP) .................................... 11382314

(51) Int. Cl.
*G01N 33/94* (2006.01)
*G01N 33/567* (2006.01)
*G01N 33/50* (2006.01)
*C07H 21/00* (2006.01)
*G01N 33/53* (2006.01)
*C07K 14/435* (2006.01)
*C07K 14/47* (2006.01)

(52) U.S. Cl.
CPC ............. *G01N 33/94* (2013.01); *G01N 33/50* (2013.01); *G01N 33/5005* (2013.01); *G01N 33/5308* (2013.01); *G01N 2496/00* (2013.01); *G01N 2560/00* (2013.01); *Y10T 436/163333* (2015.01)

(58) Field of Classification Search
USPC ............... 435/325, 6.16, 7.2; 530/350, 388.1
IPC ........ G01N 33/50; C07H 21/00; C07K 14/435, 14/47
See application file for complete search history.

(56) References Cited

PUBLICATIONS

Sato et al. 2010. Quantitative and Wide-Ranging Profiling of Phospholipids in Human Plasma by Two-dimensional Liquid Chromatography/Mass Spectrometry. Analytical Chemistry, vol. 82, pp. 9858-9864.*
Pangborn, 1942. Isolation and Purification of a Serologically Active Phospholipid From Beef Heart. Journal of Biological Chemistry, vol. 143, pp. 247-256.*
Liu et al. 2009. Simultaneous determination of inositol and inositol phosphates in complex biological matrices: quantitative ion-exchange chromatography/tandem mass spectrometry. Rapid Communications in Mass Spectrometry, vol. 23, pp. 705-712.*
Thermo Fisher Scientific (2016 Ion Exchange Column, 3 Pages.*
Gertz et al. 1995. Studies of the oral bioavailability of alendronate. Clinical Pharmacology and Therapeutics, vol. 58, No. 3, pp. 288-298.*
Kindt et al. 2004. Development and Validation of an LC/MS/MS Procedure for the Quantification of Endogenous myo-Inositol Concentrations in Rat Brain Tissue Homogenates. Analytical Chemistry, vol. 76, pp. 4901-4908.*
Woodcock, "Analysis of Inositol Phosphates in Heart Tissue Using Anion-Exchange High Performance Liquid Chromatography", 1997,Mol Cell Biochem 172; p. 121.
Pettitt, "Analysis of Intact Phosphoinositides in Biological Samples" Journal of LIPID research, vol. 47, No. 7; Jan. 1, 2006; pp. 1588-1596.
Eiseman et al "Pharmacokinetics and Tissue Distribution of Inositol Hexaphosphate in C.B17 SCID . . . " Metabolism, vol. 60, No. 10; Oct. 1, 2011, pp. 1465-1474.

(Continued)

*Primary Examiner* — Debbie K Ware
*Assistant Examiner* — Kailash C Srivastava
(74) *Attorney, Agent, or Firm* — Sterne, Kessler, Goldstein & Fox P.L.L.C.

(57) ABSTRACT

The present invention relates to method for the direct detection and/or quantification of at least one compound with a molecular weight of at least 200, wherein the compound to be detected and/or quantified is a chemically complex molecule, wherein said chemically complex molecule is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, wherein the compound or compounds to be detected and/or quantified are within a biological matrix, wherein said biological matrix is a biological fluid, a biological tissue, stomach contents, intestine contents, stool sample or a culture cells, wherein the method comprises performing a chromatography and identifying the retention time and/or the intensity of the signal by means of a mass or radioactivity detector.

9 Claims, 15 Drawing Sheets

(56) References Cited

PUBLICATIONS

Binder et al, "Separation of Inositol Phosphates and Glycerophosphoinositol Phosphates . . . " Analytical Biochemistry, Academic Press; vol. 148, No. 1, Jul. 1, 1985; pp. 220-227.
Williams et al "Measurement of Sarcoplasmic Reticulum Ca<2+> ATPase Activity . . . " Analytical Biochemistry, Academic Press; vol. 372, No. 2, Nov. 20, 2007; pp. 135-139.

* cited by examiner

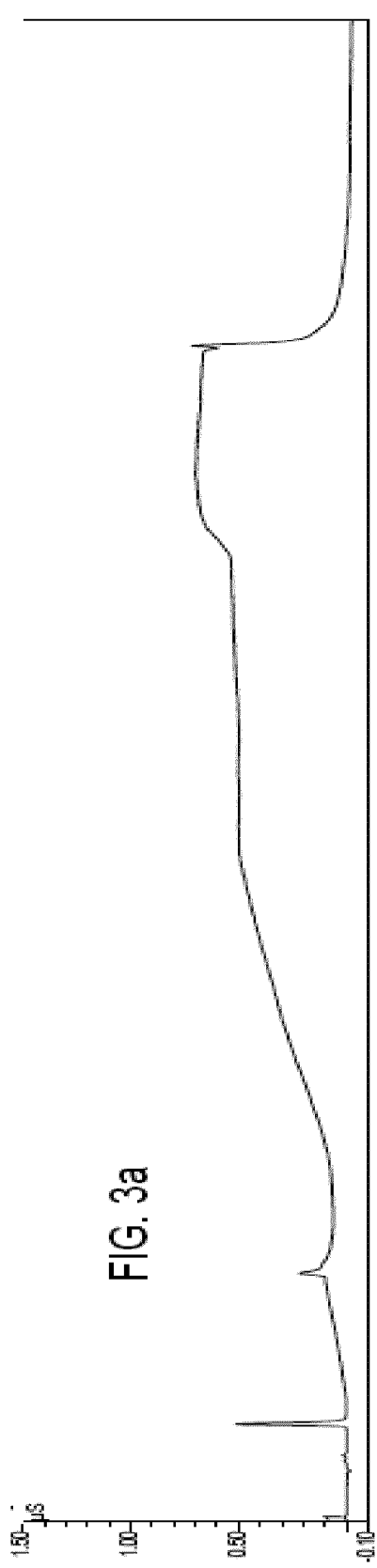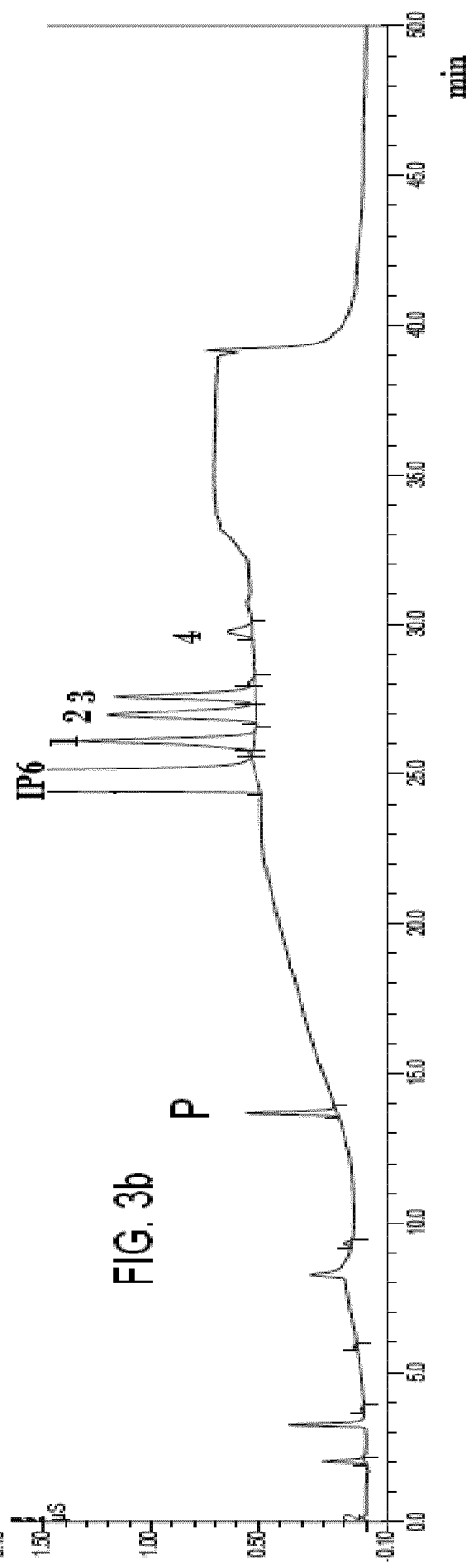

$t_R$ Phytic Acid: ≈ 4.06 min; $t_R$ m/z 779: ≈ 4.08 min; $t_R$ IP7: ≈ 4.12 min; $t_R$ IP5: ≈ 4.08 min;
$t_R$ IP4: ≈ 4.04 min; $t_R$ IP2: ≈ 4.16 min $t_R$ Phytic Acid: ≈ 4.08 min; $t_R$ *m/z 779*: ≈ 4.12 min; $t_R$ IP7: ≈ 4.12 min; $t_R$ IP5: ≈ 4.08 min; $t_R$ IP4: ≈ 4.08 min; $t_R$ IP2: ≈ 4.16 min

METHOD FOR THE DIRECT DETECTION AND/OR QUANTIFICATION OF AT LEAST ONE COMPOUND WITH A MOLECULAR WEIGHT OF AT LEAST 200

The present invention relates to a direct liquid chromatography methodology for the quantification of chemical complex molecules, especially wherein the chemically complex molecule is an inositol polyphosphate, selected from the group containing from 2 to 6 phosphate groups.

BACKGROUND ART

The analytical determination of phosphorus containing chemically complex molecules is fraught with serious difficulties due mainly to their physicochemical properties. These molecules are highly charged and due to the presence of complex functional groups, such as phosphates or phosphonates, show a different ionization degree depending on pH. This issue becomes especially relevant for molecules with more than one phosphorus containing group.

Likewise, the absorption bands lack within the UV-Vis spectrum region in the majority of these chemically complex molecules hinder its quantification by direct spectrophotometric methods.

Furthermore, the determination of chemically complex molecules within a biological matrix involves additional difficulties due to the matrix effect, so new bioanalytical methods for routine use must be developed and validated.

The low concentration of the analyte compared to other components in the matrix can suppress the analyte response. These effects can cause differences in response between sample in matrix and standards, leading to difficulties in quantitative analysis and compound identification (Biol Pharm Bull 25, 547-557; 2002).

For example, bisphosphonates present two phosphonic groups per molecule which lend a strongly ionic character and increased polarity. Additionally, the majority of the members of this family lacks of chromophores excluding convenient direct UV detection (J Pharm Biomed Anal 48, 483-496; 2008). Other bioanalytical methods have been developed for the determination of bisphosphonates, adding a derivatization step for its determination or fragmentation not being a direct method, understood direct method as the determination of the molecule per se or an adduct of this molecule, what provides a more sensible, specific, accurate, and robust method but specially more applicable, quick and reliable methodologies for routine analysis (J Chromatogr B 877, 3159-3168; 2009, Int J Mass Spectrom 295, 85-93; 2010, J Mass Spectrom 37, 197-208; 2002).

Other example of phosphorus containing chemically complex molecule are pyrophosphates. Pyrophosphates differ from the bisphosphonates in the carbon atom that binds the two phosphorus atoms (Carbon atom of the bisphosphonates (P—C—P) is replaced by an oxygen (P—O—P)).

Nucleotides are also an example of chemically complex molecules, highly charged and with polar nature (due to the presence of one or more phosphate groups), thus being this invention especially relevant for those with more than one phosphate group.

The selective determination of inositol polyphosphates (from 2 to 6 phosphate groups), together with other related impurities and especially in biological matrices is one of the major analytical breakthroughs faced in this invention. In the extreme case, inositol hexaphosphate, also known as InsP6 or IP6, presents 12 dissociable protons, having pKa values that range from negative values to more than 10 (Carbohydr Res 46, 159-171; 1976).

Numerous analytical methods for InsP6 quantification have been described in bibliography. Nevertheless, most of them have been developed for determination in simple matrices, (e.g. those that come from methods for food extracts or pharmaceutical preparations), where concentrations of InsP6 are higher than expected in biological matrices.

In the case of complex matrices (generally, those with biological origin) previous cited methods have not sensitivity and specificity enough for InsP6 determination when concentrations to be quantified are low, as the case of plasma, urine, other biological fluids, tissues or cells.

A high sensible and selective method is needed for the quantification of inositol polyphosphates in this kind of matrices, and together with their special physicochemical properties, make most of the current methods useless.

Moreover, although some of the current methods could detect inositol polyphosphates, they are not reproducible and solid enough for their use in clinical studies, when routine sample analysis must be performed.

The WO/2009/109647 discloses the determination of the amount of inositol phosphate (IP1 or InsP1, only 1 phosphate group) in the sample (urine, plasma) by using LC-ESI/MS/MS assay. The US20100136600 discloses the determination of myo-inositol in the sample (urine, plasma) by using LC-MS/HPLC-MS techniques. However, neither of them disclose the IP6 determination method and also the determination technique disclosed in these patents may not be effective/suitable for IP2-IP6 determination because IP2-IP6 are highly charged molecules as compared to the inositol (no phosphate groups, no charge) or IP1 (only one phosphate group, limited charge).

Indirect methods for the determination of InsP6 and InsP3 in plasma were previously developed by using gas chromatography-mass detection analysis of HPLC chromatographic fractions which involves hydrolysis of IP6 and further, determination of inositol or phosphate, leading to a highly time consuming methodology (3 days per sample) and poorly accurate results (Life Sci 71, 1535-1546; 2002).

Direct HPLC-MS for its quantification in plants extracts and in vitro culture cells have already been described (Mass Spectrom 23, 705-712; 2009). However, the HPLC conditions described make the method useless for all the other biological matrices.

HPLC/MS with thermospray ionization allows the determination of inositol phosphates, but the lack of sensitivity is stated in the paper as a limitation for biological applications (Biomed Environ Mass Spectrom 19, 597-600; 1990).

Other indirect methods for the determination of IP6 in human urine are based on the total phosphorus measurement of purified extracts of phytic acid are described. In this case, a specific pretreatment of the sample is required to avoid interference from other phosphorus containing compounds accompanying phytic acid in urine such as phosphate or pyrophosphate (Anal Chem 75, 6374-6378; 2003, Anal Chim Acta 510, 41-43; 2004). One of the drawbacks of these methods is that they are limited to, due to sensitivity and selectivity issues, urine samples, not being applicable to tissues or blood samples and to the quantification of related impurities. In addition, the indirect determination of IP6 through total phosphorus is an extrapolation which leads to systematic high values since all the quantified phosphorus is identified as IP6.

Another indirect method is described for the determination of phytate in human urine. The method is based on hydrolysis of the phytate and determination of myo-inositol, one of the hydrolysis products (Chromatographia 60, 265-268; 2004). This is a time-consuming methodology (2 days per sample) due to the need of acidic hydrolysis. Furthermore, the limited sensitivity and the lack of specificity of the hydrolysis make the method useless for other biological matrices and for the co-quantification of related impurities.

Other documents considered as prior art for IP6 determination in biological samples (mainly in urine) are cited below:

March et al described in 2001 a unique methodology to quantify inositol phosphates in blood, but also applicable to urine and tissues (J Chromatogr B 757, 247-255; 2001). It's a time-consuming indirect methodology (3 days per sample) based on the enzymatic hydrolysis of IP6 and determination of the inositol molecule (hydrolysate) through gas chromatography and mass spectrometry. It's a sensitive method, although indirect, based on different principles from the present invention, which in any case fails in the specificity, since all inositol phosphates are hydrolysed inespecifically and the whole hydrolysate is quantified as IP6.

Fluorescence has been widely used for the quantification of IP6, although the poor sensitivity just allows the application in foods and in urine as biological samples (Anal Chim Acta 605, 185-191; 2007).

They are totally different methods from the invention here described, which in any case fail to determine related impurities and are not applicable to other biological matrices different from urine.

SUMMARY OF THE INVENTION

The present invention relates to a direct liquid chromatography methodology for the quantification of chemical complex molecules, understood under the scope of this invention as molecules with least two phosphorus containing groups and a molecular weight of at least 200. These complex molecules are highly polar and highly charged due to the presence of several ionizable groups. In addition, in many cases the lack of absorption bands in the UV-visible spectrum region make these molecules invisible through the classical techniques.

The identification and quantification of the target compound is performed through direct detection. Under the scope of the present invention, direct detection is defined as the identification/quantification of the analyte by means of a property of the compound (or its ions or salts thereof) 'as is' or a property of the compound forming an adduct (such as but not limited to ionic associates), metabolites, preferably phase II metabolites, of the parent compound, including fragments of the main analyte in mass detection. This property measured by direct detection can be, but is not limited to, mass detection, conductivity, radioactivity (thus the analyte can be radiolabelled), NMR, being the mass detection a preferred one. The present inventors have found that, when the mass is the chemical complex molecule is lower than 200, selectivity is compromised at those levels due to the interference of several compounds from the mobile phases and the atmosphere.

In addition, the sensitivity of the present invention can be around 1 pmol, which is in the high range of the currently available methodologies. Moreover, the combination of the sensitivity with the specificity/selectivity of the present invention allows its application in all kind of biological matrices as well as the quantification of the main analyte together with related impurities in the case of quality control of active pharmaceutical ingredients (s), medical foods, reagents, food additives, pharmaceutical compositions or nutraceuticals.

"Biological matrix" refers to an environment that may or may not be isolated from a warm-blooded animal. Non-limiting examples of biological matrices are: fluid, tissue, stomach contents, intestine contents, stool sample, culture cells, urine, feces, blood, serum, plasma, saliva, perspiration, tissue fluid, cellular cytoplasm, hepatocytes, microsomes, S9 fractions, tissues, such as muscle tissue, hepatic tissue, cardiac tissue, renal tissue and other bodily environments and/or matrices of a warm-blooded animal, preferably a human. A biological matrix may be present in solution or in solid form or a mixture thereof and may be present in or as part of a living organism or may be isolated from a living organism such that it forms a sample therefrom. The methods herein disclosed provide excellent results even working with a biological matrix comprising very low levels of chemically complex molecule, being preferred concentrations those below 0.001 μmol/mg (for solid matrices) or μmol/μl (for matrices in other physical states), even more preferred below 0.000001 μmol/mg or μmol/μl, and even more preferred amounts in the range of 0.0000001 μmol/mg or μg/μl. The biological matrix may be biological fluids, which can be, but are not limited to, blood, plasma, serum, urine, saliva, lymphatic liquid, cerebrospinal fluid and mixtures thereof, preferably blood or plasma. The biological matrix may be also a biological tissue, which can be, but is not limited to lung, liver, kidney, heart, blood vessels, brain, bone, skin, muscle, nervous tissue, vascular tissue and mixtures thereof, preferably heart tissue.

The method as herein disclosed, it is also a reliable methodology for biological matrices of different species, for example, but not limited to, rats, mice, dogs, monkeys, humans, pigs, minipigs, rabbits, guinea pigs.

Various aspects of the present invention are described below.

Therefore, the method as herein disclosed provides a method for the direct detection and/or quantification of at least one compound with a molecular weight of at least 200, wherein the compound to be detected and/or quantified is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein the compound or compounds to be detected and/or quantified are within a biological matrix, wherein said biological matrix is a biological fluid, a biological tissue, stomach contents, intestine contents, stool sample or a culture cells, wherein the method comprises performing a chromatography and identifying the retention time and/or the intensity of the signal by means of a mass or radioactivity detector.

According to the first aspect of the present invention there is provided a method for the direct detection and/or quantification of at least one compound with a molecular weight of at least 200, wherein the compound to be detected and/or quantified is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein the compound or compounds to be detected and/or quantified are within a biological matrix, wherein said biological matrix is a biological fluid, a biological tissue, stomach contents, intestine contents, stool sample or a culture cells, wherein the method for the direct detection and/or quantification comprises at least the following steps:

i) preparing at least one standard sample, preferably of a known concentration or from a known concentration, of the chemically complex molecule to be detected and/or quantified;

ii) introducing the standard sample into the stream of a solvent system; wherein the solvent system is a polar solvent or a solvent mixture comprising at least one polar solvent; wherein the pH of at least one solvent which forms the solvent system has been preferably buffered, between 7 and 14.

iii) passing the sample and the solvent system through at least one chromatographic column wherein the column is essentially filled of smalls particles of a stationary phase, preferably a non-polar stationary phase, while maintaining the pressure of the system between 5 and 1500 atm;

iv) identifying the retention time and/or quantifying the intensity of the signal of when the chemically complex molecule is eluated, by means of a mass or radioactivity detector;

v) preparing a sample of the chemically complex molecule from a biological matrix comprising the chemically complex molecule to be detected and/or quantified, wherein the process to prepare the sample comprises at least dissolving totally or partially the biological matrix to form a solution or a slurry, and, if necessary treating the solution or the slurry to remove particles in suspension;

vi) repeating the steps (ii) and (iii) with the sample prepared in the step (v); together or sequentially with the standard vii) detecting and/or quantifying the presence of the chemically complex molecule by comparison of retention time and/or intensity of signal of the standard sample or the standard samples, or by comparison of retention time and/or intensity of signal obtained from previous studies or from literature.

According to the second aspect of the present invention there is provided a method for analysing an API, a medical food, a reagent, a food additive, a pharmaceutical composition or nutraceutical, wherein the API, the medical food, the reagent, the food additive, the pharmaceutical composition or the nutraceutical comprise at least one compound with a molecular weight of at least 200, wherein said compound is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein this compound can also be quantified together with its related impurities, wherein the method for analysing comprises at least the following steps:

i) preparing at least one standard sample, preferably of a known concentration or from a known concentration of the chemically complex molecule to be detected and/or quantified;

ii) introducing the standard sample into the stream of a solvent system; wherein the solvent system is a polar solvent or a solvent mixture comprising at least one polar solvent; wherein the pH of at least one solvent which forms the solvent system has been preferably buffered, between 7 and 14.

iii) passing the sample and the solvent system through at least one chromatographic column wherein the column is essentially filled of smalls particles of a stationary phase, preferably a non-polar stationary phase, while maintaining the pressure of the system between 5 and 1500 atm;

iv) identifying the retention time and/or quantifying the intensity of the signal of when the chemically complex molecule is eluated, by means of a detector capable to detect the eluation of the chemically complex molecule;

v) preparing a sample of the chemically complex molecule from the API, a medical food, a reagent, a food additive, a pharmaceutical composition or nutraceutical comprising the chemically complex molecule to be detected and/or quantified, wherein the process to prepare the sample comprises at least dissolving totally or partially the API, medical food, reagent, food additive, pharmaceutical composition or nutraceutical to form a solution or a slurry, and, if necessary, treating the solution or the slurry to remove particles in suspension;

vi) repeating the steps (ii) and (iii) with the sample prepared in the step (v); together or sequentially with the standard.

vii) detecting and/or quantifying the presence of the chemically complex molecule by comparison of retention time and/or intensity of signal of the standard sample or the standard samples, or by comparison of retention time and/or intensity of signal obtained from previous studies or from literature.

According to the third aspect of the present invention there is provide a process for preparing a drug, a medical food, a pharmaceutical composition or a nutraceutical pharmaceutical composition comprising at least one compound with a molecular weight of at least 200, wherein said compound is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein the drug, a medical food, a pharmaceutical composition or a nutraceutical has to have a predetermined percentage of the chemically complex molecule, wherein the process comprises: obtaining a batch of a drug, a medical food, a pharmaceutical composition or a nutraceutical pharmaceutical; measuring the percentage of purity the chemically complex molecule of the batch by a process comprising the method according to the second aspect; and including the drug, the medical food, the pharmaceutical composition or the nutraceutical batch only if its percentage of the chemical complex molecule so measured is within the requirements or predefined specifications, being the normal assay, referred to dry content, major than 60%, preferably major than 70% and more preferably major than 80%.

According to the fourth aspect of the present invention there is provided a process for the production of a pharmaceutical composition comprising at least one compound with a molecular weight of at least 200, wherein said compound is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein the process comprises essentially the same process steps of a process for the production of a first batch, provided that after analyzing by any of the method of the first aspect a biological isolated sample, preferably a blood or a serum sample, taken from subjects to whom the pharmaceutical compositions obtained by the first batch were administrated, the calculated AUC and Cmax are within the desire requirements and/or are bioequivalent to a reference drug, medical food, pharmaceutical composition or nutraceutical. "AUC" refers to the area under a curve representing the concentration of a compound or metabolite thereof in a biological fluid, e.g., plasma and blood, in a patient as a function of time following administration of the compound to the patient. Cmax is the maximum concentration of a drug in the plasma or blood of a patient following administration of a dose of the drug or form of drug to the patient.

DETAILED DESCRIPTION OF THE INVENTION

Various embodiments of the present invention are described below.

The chemically complex molecule may be a bisphosphonate, hexametaphosphate or a C3-C7 cycloalkyl, wherein said C3-C7 cycloalkyl is substituted with at least two groups —R, with the proviso that at least two R are independently selected from —P(O)(OH)2 and —OP(O)(OH)2. The term "C3-C7 cycloalkyl" refers to saturated cyclic alkyl group having from three to seven carbon atoms and includes cyclopropyl, cyclobutyl, cyclopentyl, cyclohexyl, and cycloheptyl. Preferred chemically complex molecule is a C6 cycloalkyl. The chemically complex molecule may be also a cycloalkyl derivative. Excellent results have been achieved when the chemically complex molecule is an inositol polyphosphate.

The chemically complex molecule may be radiolabelled.

The standard sample prepared in step (ii) may be a reference standard, external standard, internal standard or standard addition, meaning this latter a standard prepared by the standard addition method, also described below.

As used herein, the term "reference standard" refers to a compound that may be used both for quantitative and qualitative analysis of an analyte, which could be, but not limited to, an active pharmaceutical ingredient. For example, the retention time of the compound in liquid chromatography (LC), for example HPLC or UPLC, allows for setting a relative retention time, thus making qualitative analysis possible. The concentration of the compound in solution before injection into an LC column allows for comparison of the areas under the peaks in an LC chromatogram, thus making quantitative analysis possible.

As used herein, the term external standard refers to a chemical complex molecule of known concentration. If used for determining concentration, external standards may be preferably added to the test sample at a known concentration, technique known as standard addition.

As used herein, the term "internal standard" refers to what is added to and subsequently detected and quantified in the sample. The addition of the internal standard can be before, during or after sample collection or processing. The internal standard, as contemplated by the present invention, is a compound that is added to the sample, and this similar compound is then quantified using the methods described herein.

The solvent system preferably comprises a polar organic solvent. Solvent system comprises a water-miscible polar organic solvent are of particular interest. Preferred solvent systems comprise acetonitrile, methanol or mixtures thereof. More preferably the solvent system comprises acetonitrile.

Additionally the solvent system may comprise water. One of the most preferred solvent systems comprises, preferably consisting essentially of, water and acetonitrile.

The solvent system may be isocratic or gradient. In one preferred embodiment during the step (iii) the composition of the solvent system is gradually increased, i.e. gradient, i.e. the strength of the mobile phase is gradually increased. Preferably the system starts with a high water content at the moment when the sample and the solvent system start passing throughout the column and then the water content is gradually decreased during the elution of the chemically complex molecule.

Optionally, during the step (iii) the composition of the solvent system and consequently the strength of the mobile phase is maintained essentially unaltered.

In one particular embodiment, during the step (iii) the solvent system comprises at least one solvent, wherein the pH of such solvent has been buffered from 7 to 14, preferably the pH of such solvent has been adjusted from 8 to 13, and more preferably from 8.5 to 12.

There are several techniques available to the skilled person to adjust the pH. The pH could be modified with a substance capable of modifying the pH, typically, but not limited to, an acid, a base or a salt with acidic or basic properties. Amongst other, substances capable of modifying the pH can be an amine, an inorganic base, a salt of an organic acid, or any mixtures thereof. Amine and, particularly triethylamine, are preferred. The inorganic base may be a hydroxide, preferably KOH. It could be used as a salt of an organic acid, e.g. acetate.

In a particular embodiment, before injecting the already prepared sample to the corresponding equipment, there is an additional pH control. Preferably, the pH is adjusted to the same pH as the mobile phase. It can be adjusted with an acid, a base or a salt, preferably an amine base, and more preferably the amine is triethylamine.

As used herein, the term "chromatographic column" refers to a tube packed with adsorbent particles and used to perform chromatography. Particularly interesting are column wherein the smalls particles of a non-polar stationary phase are silica based, preferably silica gel based. Good results are obtained when the smalls particles are a non-polar stationary phase, preferably are silica gel based covalently bonded to an alkyl chain group. The alkyl chain group may be a $C_2$-$C_{20}$ alkyl, preferably a $C_8$-$C_{18}$ alkyl.

The small particles of a non-polar stationary phase may have a mean particle size between 0.5 and 20 microns, preferably between 1.5 and 15, even more preferably between 5 and 10.

The pore size may range between 10 and 1000 Angstroms, preferably between 60 and 500 Angstroms, and even more preferably between 100 and 300 Angstroms.

The reproducibility of the system and other advantages are improved when the temperature of the column during the step (iii) is maintained essentially unaltered. Typically the temperature of the column during the step (iii) is maintained essentially unaltered between 10 and 70° C. Preferably, it is maintained essentially unaltered between 45 and 55° C., and more preferably is maintained essentially unaltered about 50° C.

The term "detector" refers to any device, apparatus, machine, component, or system that can detect the chemical complex molecule. Detectors may or may not include hardware and software. In a mass detector (mass spectrometer) the common detector includes and/or is coupled to a mass analyzer. Examples of detectors capable to detect the eluation of the chemically complex molecule is a mass spectrometers; a tandem mass spectrometer (or triple quadrupole); a single quadrupole. These mass detectors can work with several operating modes, amongst others selected ion monitoring (SIM), multiple reaction monitoring (MRM), selected reaction monitoring (SRM) and SCAN (negative/positive); or several of them. A radioactivity detector can also be used. For the second aspect, it is also possible to use a conductimetry, photometric and/or a NMR detector.

The use of mass detector typically implies a further step, namely a previous step of phase change and ionization after the chemically complex molecule between the elution and the detection. The phase change and ionization may be, but not limited to, a chemical ionization (APCI), atmospheric pressure photoionization (APPI) or electrospray ionization (ESI) or thermospray. The electrospray ionization (ESI) may be carried out under $N_2$ at a temperature between 250 and 1000° C., preferably between 300 an 800° C., even more preferably between 400 and 600° C.

For pretreating the biological sample it may be necessary in the step (v) the use of a protein precipitating agent, preferably trichloroacetic acid for the pretreatment of the sample. This additional treatment allows the simplification of the biological matrix, obtaining better selectivity and increasing sensitivity, by reducing matrix effects. Step (v) may also comprise the use of a chelating agent for the pretreatment of the sample, such as EDTA. These chelating agents reduce the free calcium concentration in the biological sample, thus avoiding the formation of labile compounds together with the analyte, which would reduce the recuperation and compromise the accuracy of the methodology.

The biological matrix may be also preconcentrated, thus increasing the sensitivity of the method.

In another particular embodiment there is provided a method for the direct detection and/or quantification of an inositol polyphosphate containing at least 2 phosphorus groups, or its ions or salts thereof, wherein the inositol polyphosphate is within a biological matrix, wherein said biological matrix is a biological fluid, a biological tissue, stomach contents, intestine contents, stool sample or a culture cells, wherein the method for the direct detection and/or quantification comprises at least the following steps:
i) preparing at least one standard sample, preferably of a known concentration or from a known concentration, of inositol polyphosphate containing at least 2 phosphorus groups to be detected and/or quantified;
ii) introducing the standard sample into the stream of a solvent system; wherein the solvent system consists of an aqueous solution of an amine; wherein the pH of the solvent has been buffered, between 8 and 13.
iii) passing the sample and the solvent system through at least one column wherein the column is a reversed-phase stationary phase, being the particle size between 1.5-15 microns and the pore size between 60-500 Angstroms.
iv) identifying the retention time and/or quantifying the intensity of the signal of when the inositol polyphosphate is eluated, by means of a mass detector;
v) preparing a sample of the inositol polyphoshate from a biological matrix comprising the inositol polyphoshate to be detected and/or quantified, wherein the process to prepare the sample comprises at least dissolving totally or partially the biological matrix to form a solution or a slurry, and, if necessary treating the solution or the slurry to remove particles in suspension;
vi) repeating the steps (ii) and (iii) with the sample prepared in the step (v); together or sequentially with the standard.
vii) detecting and/or quantifying the presence of the inositol polyphoshate by comparison of retention time and/or intensity of signal of the standard sample or the standard samples.

During the sample pretreatment, a step for solid-liquid separation may be included, typically centrifugation or filtration, to remove any solid particles that could have appeared during the process. In this step the temperature is preferably controlled to 2-8° C. during the sample pretreatment, more preferably about 4° C.

The method as disclosed herein is useful for the analysis of chemical complex molecules. One particular use of the methods as disclosed herein is analysis of biologically matrix of human beings when the human being is under a bioequivalence study. Another particular use of the methods as disclosed herein is to simultaneously determine related impurities of the chemical complex molecule, especially of IP6.

The method of the present invention may be combined with other analytical techniques (RMN/Karl Fischer/GC/ICP/TG).

The term "metabolic profile" comprises the identification, semi-quantification and/or quantification of one or more metabolites derived from a parent compound, in a biological matrix, which mainly consist of phosphorylation-dephosphorilation metabolic pathways.

The term "impurities profile" comprises the identification, semi-quantification and/or quantification of one or more impurities derived from a parent compound, mainly dephosphorylation related impurities, in a formulation of an API, a medical food, a reagent, a food additive, a pharmaceutical composition or nutraceutical.

Further aspects/embodiments of the present invention can be found in the following clauses:

Clause 1.—Method for the direct detection and/or quantification of at least one compound with a molecular weight of at least 200, wherein the compound to be detected and/or quantified is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein the compound or compounds to be detected and/or quantified are within a biological matrix, wherein said biological matrix is a biological fluid, a biological tissue, stomach contents, intestine contents, stool sample or a culture cells, wherein the method for the direct detection and/or quantification comprises at least the following steps:
i) preparing at least one standard sample, preferably of a known concentration or from a known concentration, of the chemically complex molecule to be detected and/or quantified;
ii) introducing the standard sample into the stream of a solvent system; wherein the solvent system is a polar solvent or a solvent mixture comprising at least one polar solvent; wherein the pH of at least one solvent which forms the solvent system has been preferably buffered, between 7 and 14.
iii) passing the sample and the solvent system through at least one column wherein the column is essentially filled of smalls particles of a stationary phase, preferably a non-polar stationary phase, while maintaining the pressure of the system between 5 and 1500 atm;

iv) indentifying the retention time and/or quantifying the intensity of the signal of when the chemically complex molecule is eluated, by means of a mass or radioactivity detector;

v) preparing a sample of the chemically complex molecule from a biological matrix comprising the chemically complex molecule to be detected and/or quantified, wherein the process to prepare the sample comprises at least dissolving totally or partially the biological matrix to form a solution or a slurry, and, if necessary treating the solution or the slurry to remove particles in suspension;

vi) repeating the steps (ii) and (iii) with the sample prepared in the step (v); together or sequentially with the standard.

vii) detecting and/or quantifying the presence of the chemically complex molecule by comparison of retention time and/or intensity of signal of the standard sample or the standard samples, or by comparison of retention time and/or intensity of signal obtained from previous studies or from literature.

Clause 2.—The method according to the preceding clause, wherein the chemically complex molecule is a bis-phosphonate, hexametaphosphate, nucleotide or a C3-C7 cycloalkyl, wherein said C3-C7 cycloalkyl is substituted with at least two groups —R.

Clause 3.—The method according to any one of the preceding clauses, wherein the chemically complex molecule is an inositol polyphosphate, selected from the group containing from 2 to 6 phosphate groups.

Clause 4.—The method according to any one of the preceding clauses, wherein the standard sample prepared in step (ii) is a reference standard, external standard, internal standard or standard addition Clause 5.—The method according to any one of the preceding clauses, wherein the solvent system comprises a water-miscible polar organic solvent.

Clause 6.—The method according to any one of the preceding clauses, wherein during the step (iii) the composition of the solvent system is gradually increased, i.e. the strength of the mobile phase is gradually increased.

Clause 7.—The method according to any one of the clauses 1 to 5, wherein during the step (iii) the composition of the solvent system is the strength of the mobile phase is maintained essentially unaltered.

Clause 8.—The method according to any one of the preceding clauses, wherein the solvent system comprises water, and the pH of the water has been adjusted from 7 to 14, preferably from 8 to 13, and more preferably from 8.5 to 12 with a substance capable of modifying the pH, wherein the substance capable of modifying the pH is preferably an amine, an inorganic base, a salt of an organic acid, or any mixtures thereof, more preferably an amine and/or $NH_3$, a salt of an organic acid or an hydroxide, and even more preferably triethylamine and/or $NH_3$.

Clause 9.—The method according to any one of the preceding clauses, further comprising at least 1 additional step of pH control, preferably during the pretreatment of the sample before injecting into the equipment.

Clause 10.—The method according to any one of the preceding clauses, wherein the smalls particles of a non-polar stationary phase are silica gel based covalently bonded to an alkyl chain group, wherein alkyl chain group is preferably a $C_2$-$C_{20}$ alkyl, and more preferably a $C_8$-$C_{18}$ alkyl.

Clause 11.—The method according to any one of the preceding clauses, wherein the detector capable to detect the eluation of the chemically complex molecule is a mass spectrometer: a tandem mass spectrometer (or triple quadrupole); a single quadrupole; working under any of the following operating modes: selected ion monitoring (SIM); multiple reaction monitoring (MRM); selected reaction monitoring (SRM) and SCAN (negative/positive); or a combination of them.

Clause 12.—The method according to the preceding clause, further comprising a previous step of phase change and ionization of the chemically complex molecule between the elution and the detection.

Clause 13.—The method according to the preceding clause, wherein the phase change and ionization is chemical ionization (APCI), atmospheric pressure photoionization (APPI), electrospray ionization (ESI) or thermospray.

Clause 14.—The method according to the preceding clause, wherein the electrospray ionization (ESI) is carried out under $N_2$ at a temperature between 250 and 1000° C., preferably between 300 an 800° C., even more preferably between 400 and 600° C.

Clause 15.—The method according to any one of the preceding clauses, wherein the step (v) also comprises the use of a protein precipitating agent, preferably trichloroacetic acid for the pretreatment of the sample.

Clause 16.—The method according to any one of the preceding clauses, wherein the step (v) also comprises the use of a chelating agent for the pretreatment of the sample, preferably EDTA or its salts or any mixture thereof.

Clause 17.—The method according to any of the preceding clauses, wherein the biological matrix is preconcentrated.

Clause 18.—The method according to any of the preceding clauses further comprising a step for solid-liquid separation during the pretreatment of the sample.

Clause 19.—The method according to any one of the preceding clauses, wherein the biological matrix is a biological fluid, preferably selected from the list consisting of blood, plasma, serum, urine, saliva, lymphatic liquid, cerebrospinal fluid and mixtures thereof, preferably blood and plasma.

Clause 20.—The method according to clauses 1 to 18, wherein the biological matrix is a biological tissue, preferably selected from the list consisting of lung, kidney, heart, brain, liver, blood vessels, bone, skin, muscle, nervous tissue, vascular tissue and mixtures thereof, preferably heart tissue.

Clause 21.—The method according to any one of the preceding clauses, wherein the biologically matrix to be analysed is an isolated sample of a human being who is under an bioequivalence study.

Clause 23.—The method according to any of the preceding clauses, wherein a surrogate matrix is used to prepare the calibration curve, preferably the matrix used is formed by bovine serum albumin.

Clause 24.—The method according to any of the preceding clauses, when it is used to detect and quantify any of the metabolites of a compound in a metabolic profile.

Clause 25.—The method according to any one of the preceding clauses, wherein the compound is radiolabelled.

Clause 26.—Method for analysing an API, a medical food, a reagent, a food additive, a pharmaceutical composition or nutraceutical, wherein the API, the medical food, the pharmaceutical composition or the nutraceutical comprise at least one compound with a molecular weight of at least 200, wherein said compound is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, this compound can also be quantified together with its related impurities, wherein the method for analysing comprises at least the following steps:

i) preparing at least one standard sample, preferably of a known concentration or from a known concentration of the chemically complex molecule to be detected and/or quantified;

ii) introducing the standard sample into the stream of a solvent system; wherein the solvent system is a polar solvent or a solvent mixture comprising at least one polar solvent; wherein the pH of at least one solvent which forms the solvent system has been preferably buffered.

iii) passing the sample and the solvent system through at least one column wherein the column is essentially filled of smalls particles of a stationary phase, preferably a non-polar stationary phase, while maintaining the pressure of the system between 5 and 1500 atm;

iv) indentifying the retention time and/or quantifying the intensity of the signal of when the chemically complex molecule is eluated, by means of a detector capable to detect the eluation of the chemically complex molecule;

v) preparing a sample of the chemically complex molecule from the API, a medical food, a reagent, a food additive, a pharmaceutical composition or nutraceutical comprising the chemically complex molecule to be detected and/or quantified, wherein the process to prepare the sample comprises at least dissolving totally or partially the API, a pharmaceutical composition or nutraceutical to form a solution or a slurry, and, if necessary, treating the solution or the slurry to remove particles in suspension;

vi) repeating the steps (ii) and (iii) with the sample prepared in the step (v); together or sequentially with the standard.

vii) detecting and/or quantifying the presence of the chemically complex molecule by comparison of retention time and/or intensity of signal of the standard sample or the standard samples.

Clause 27.—The method according to the preceding clause, when it is used to detect and quantify any of the impurities of a compound in an impurities profile.

Clause 28.—A process for preparing a drug, a medical food, a reagent, a food additive, a pharmaceutical composition or a nutraceutical pharmaceutical composition comprising at least one compound with a molecular weight of at least 200, wherein said compound is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein the drug, a medical food, a pharmaceutical composition or a nutraceutical has to have a predetermined percentage of the chemically complex molecule, wherein the process comprises: obtaining a batch of a drug, a medical food, a pharmaceutical composition or a nutraceutical pharmaceutical; measuring the percentage of purity the chemically complex molecule of the batch by a process comprising the method according to the preceding clause; and including the drug, the medical food, the pharmaceutical composition or the nutraceutical batch only if its percentage of the chemical complex molecule so measured is within the requirements or specifications, preferably major than 70% by weight, and more preferably major than 80% by weight (referred to dry content)

Clause 29.—A process for the production of a pharmaceutical composition comprising at least one compound with a molecular weight of at least 200, wherein said compound is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein the process comprises essentially the same process steps of a process for the production of a first batch, provided that after analysing a biological isolated sample by any of the method of clauses 1 to 22, preferably a blood or a serum sample, taken from subjects to whom the pharmaceutical compositions obtained by the first batch were administrated, the calculated AUC and Cmax are within the desire requirements and/or are bioequivalent to a reference drug.

Clause 30.—Metabolic profile of a compound with a molecular weight of at least 200, wherein the compound to be detected and/or quantified is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein the compound or compounds are within a biological matrix, wherein said biological matrix is a biological fluid, a biological tissue, stomach contents, intestine contents, stool sample or a culture cells.

Clause 31.—Impurities profile of a compound with a molecular weight of at least 200, wherein the compound to be detected and/or quantified is a chemically complex molecule, wherein said chemically complex molecule is substituted with at least two groups —R, preferably a C3-C7 cycloalkyl, wherein said C3-C7 cycloalkyl is substituted with at least two groups —R, wherein each R group means independently —OH, —OP(O)(OH)2 or —P(O)(OH)2, with the proviso that at least two R are independently selected from —P(O)(OH)2 and —OP(O)(OH)2, including ions or salts thereof, wherein the compound or compounds are present in a formulation of an an API, a medical food, a reagent, a food additive, a pharmaceutical composition or nutraceutical

DESCRIPTION OF THE FIGURES

FIG. 3. Typical Chromatogram of an API sample (detail in the case of the sample) of example 8 (impurities profile). FIG. 3a: Blank. FIG. 3b: Sample (P: Phosphate, IP6: inositol hexaphosphate; 1, 2, 3 and 4: Related impurities).

The following examples illustrate the invention as disclosed herein and are not intended to limit the scope of the invention set forth in the claims appended thereto.

EXAMPLES

Example 1

Determination of IP6 in Rat Plasma Samples (SIM Mode)

The plasma sample underwent a purification and extraction of the compound by protein precipitation with TCA in presence of a chelating agent (EDTA). The supernatant was then diluted with trietylamine acetate (TEAA) and 20 µL was injected into UPLC®-MS system.

The ionization of phytic acid was assessed using negative electrospray ionization-mass spectrometry (ESI-MS).

Quantitative analysis was performed by mass spectrometry in the selected ion monitoring (SIM).

Figure 1:
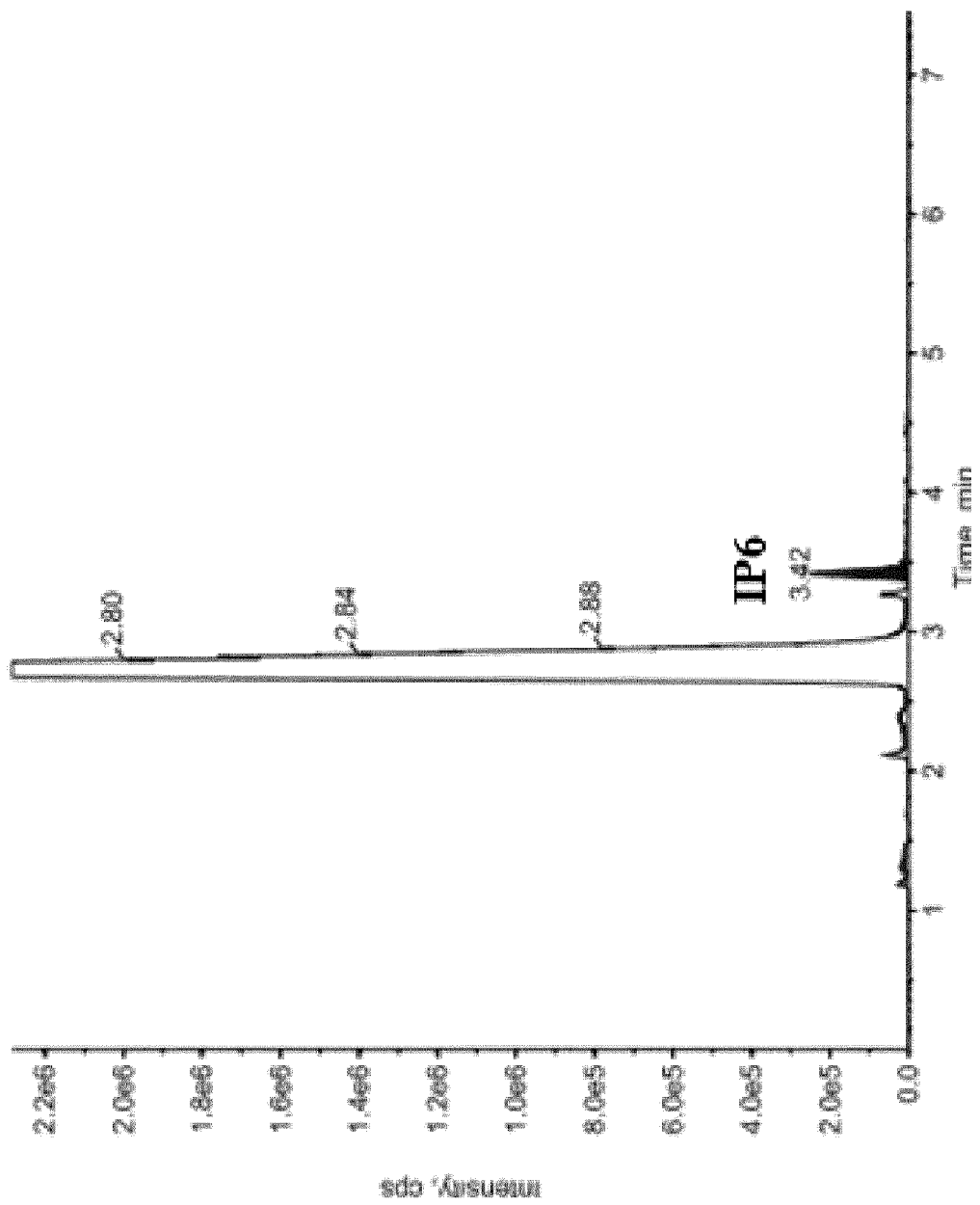
FIG. 1. UPLC®-MS chromatogram obtained for IP6 in rat plasma after gradient-elution reversed-phase chromatography of example 1.
Figure 2:
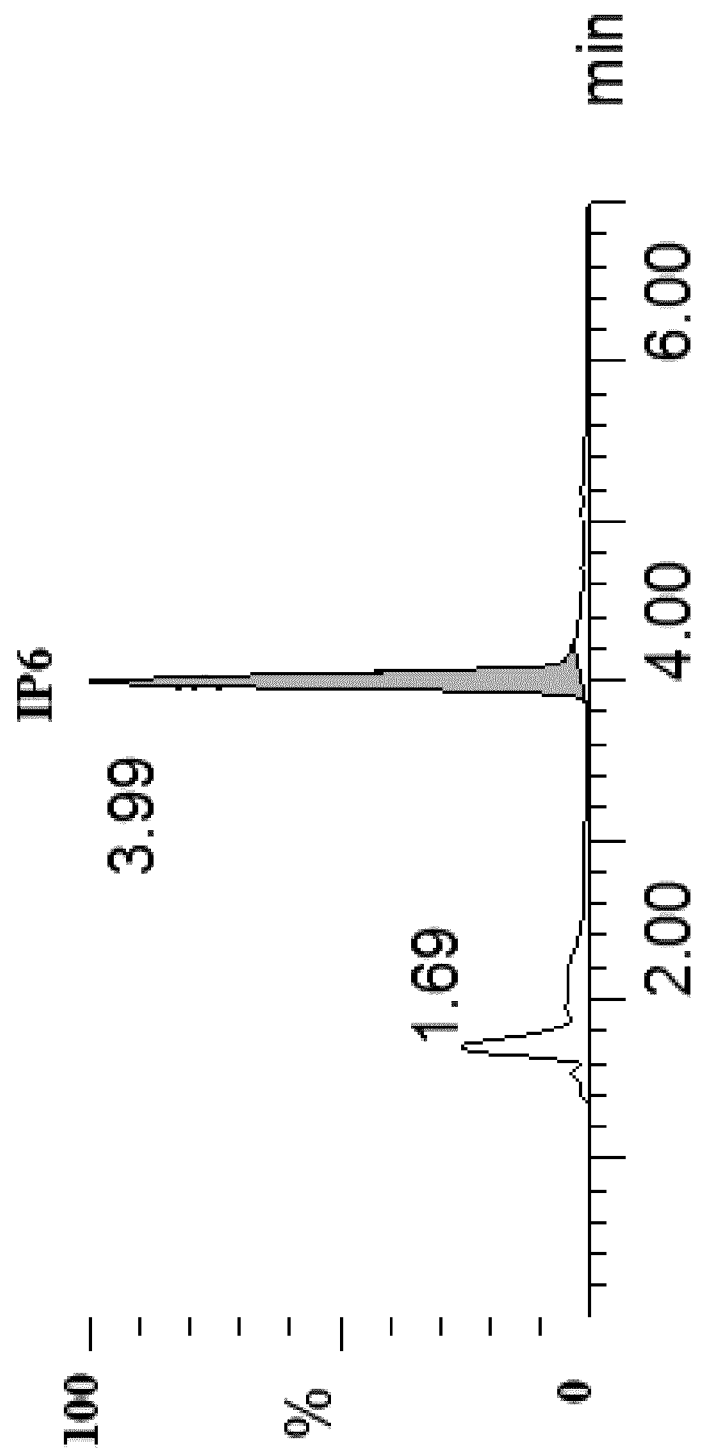
FIG. 2. HPLC-MS chromatogram obtained for IP6 in rat urine after gradient-elution reversed-phase chromatography of example 4.

The compound was analyzed by gradient-elution reversed-phase chromatography using TEAA in aqueous solution and acetonitrile as mobile phase. The retention time of the analyte under the optimized chromatographic conditions is 3.42 min (see chromatogram FIG. 1)

Example 2

Determination of IP6 in Dog Plasma Samples (SIM Mode)

The bioanalytical procedure developed in Example 1, was revalidated in dog plasma samples with a full assessment of linearity, accuracy and precision. The calibration curve was developed by injecting 20 µl of blank plasma samples spiked with a known amount of IP6. Accuracy below 10% and precision below 15% at intermediate concentrations was obtained, resulting in an excellent bioanalytical method.

Example 3

Determination of IP6 in Human Plasma Samples (SIM Mode)

The bioanalytical procedure developed in Example 1 was applied in human plasma samples, but doubling the amounts of trichloroacetic acid (TCA), matrix and chelating agent. The retention time of the analyte under the optimized chromatographic conditions was 4.05 min.

Example 4

Determination of IP6 in Rat Urine Samples (SIM Mode)

The bioanalytical procedure involved an extraction of the compound by diluting the rat urine in presence of a chelating agent (EDTA) and no precipitating agent was needed. The supernatant was then diluted with trietylamine acetate (TEAA) and 50 µL was injected into the HPLC-MS system.

The ionization of Phytic acid was assessed using negative electrospray ionization-mass spectrometry (ESI-MS). Quantitative analysis was performed by mass spectrometry in the selected ion monitoring (SIM) mode.

The compound was analyzed by gradient-elution reversed-phase chromatography, using TEAA in aqueous solution and acetonitrile as mobile phase. The retention time of the analyte under the optimized chromatographic conditions was ~3.99 min (see FIG. 3 for the chromatogram)

Example 5

Determination of IP6 in Formulations (SIM Mode)

IP6 has been identified and quantified in formulations (solutions) of the active pharmaceutical ingredient. In this example, no simultaneous quantification of related impurities is performed. The solution media consisted of water, 0.9% NaCl or other aqueous solutions as vehicle.

The determination and quantification of IP6 was developed using the same procedure as in Example 1, without any sample pretreatment apart from diluting the formulation to fit within the calibration curve range.

The validated analytical method was also used to evaluate the stability as well as the homogeneity of IP6 in unfiltered formulations. The method was proved to be lineal and specific.

Example 6

Determination of IP6 in Hepatocytes Culture Cells (SIM Mode)

The method described in Example 1 was successfully applied to hepatocytes culture cells. The study of the injection of several culture cells with a known amount of IP6 to the HPLC-MS showed a reliable method for this kind of matrix.

Example 7

Determination of IP6 in Pig Plasma Samples (SIM Mode)

The bioanalytical procedure developed in Example 1, was applied to pig plasma samples. The calibration curve was developed by injecting 50 μL of blank plasma samples spiked with a known amount of IP6. An accuracy and precision below 15% was obtained, resulting in an excellent bioanalytical method.

Example 8

Determination of IP6 and Related Impurities in Formulations

IP6 has been identified and quantified in formulations (solutions) of the active pharmaceutical ingredient. In this example, simultaneous determination of related impurities is performed, allowing the calculation of the chromatographic purity of the API.

The determination and quantification of IP6 was developed using potassium hydroxide was used as mobile phase. Sodium hydroxide can be alternatively used and the addition of small proportions of isopropanol is strongly recommended.

The used column was a anion-exchange divinyl benzene polymer. The flow rate was maintained at 1 mL/min with a temperature of 35° C.

Better sensitivity, especially for impurities, was obtained when using chemical or electrochemical ionic suppression.

Figure 4:
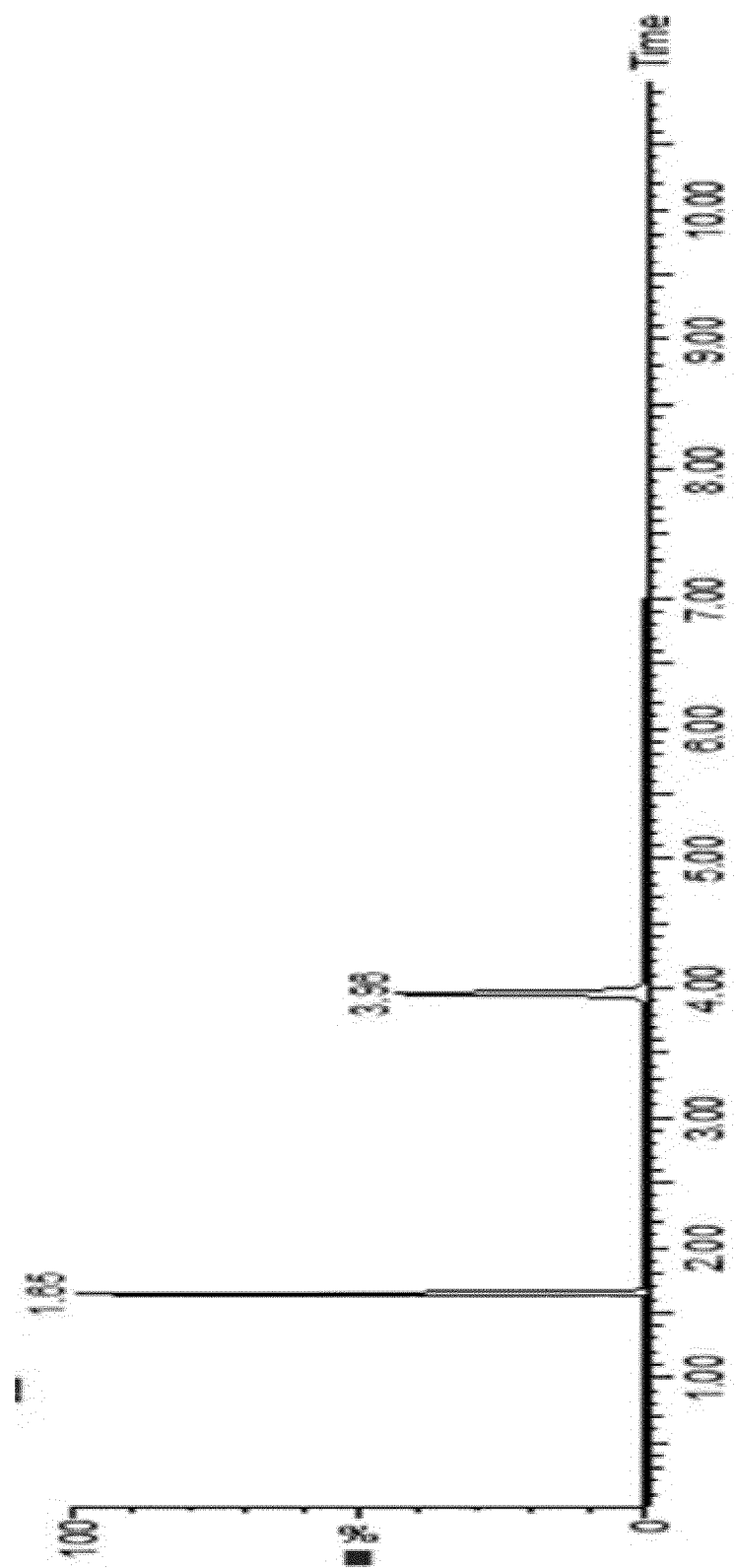
FIG. 4. Typical Chromatogram of ATP for a plasma rat sample (Example 9).

The retention time for phytic acid was 24.6 minutes (see FIG. 4). The identity of IP6 is confirmed if the retention time of the main peak in the assay sample is within ±0.5 minutes of the mean retention time of the peak corresponding to phytate for all injections of the assay working standard. This technique allows the simultaneous determination of the API together with its related impurities in a single chromatogram run.

Example 9

Determination of ATP (Adenosine Triphosphate) in Rat Plasma Samples (SIM Mode)

The bioanalytical procedure developed in Example 1, was applied to rat plasma samples, but changing the monitored mass in the SIM mode with the molecular weigh (M-1) of ATP. The calibration curve was developed by injecting 50 μl of blank plasma samples spiked with a known amount of ATP. The retention time for ATP was 3.96 min. FIG. 4 shows a typical chromatogram obtained with these samples.

Example 10

Determination of IP3 (Inositol Triphosphate) in Rat Plasma Samples (SIM Mode)

Figure 5:
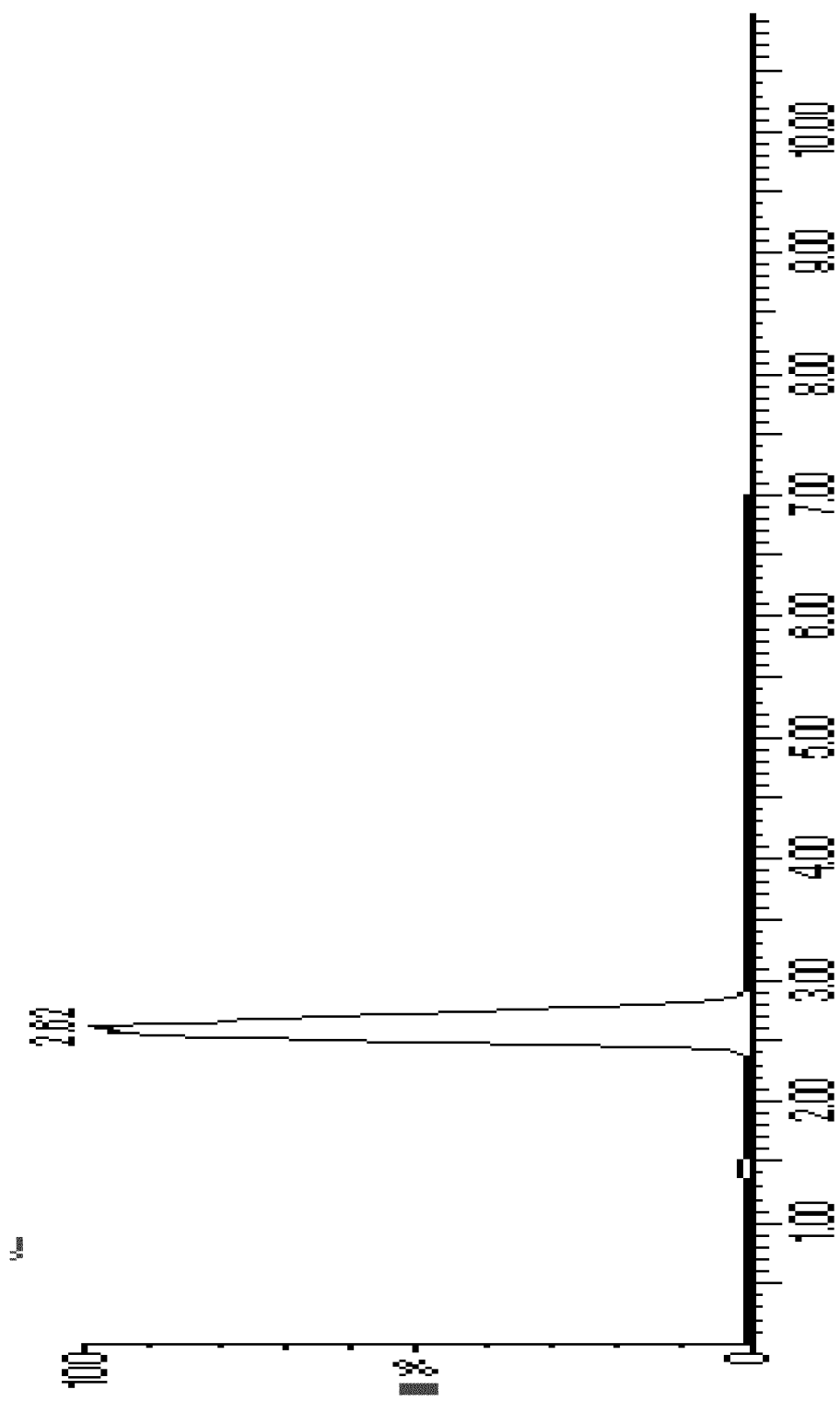
FIG. 5. Typical Chromatogram of IP3 for a plasma rat sample (Example 10).

The bioanalytical procedure developed in Example 1, was applied to rat plasma samples, but changing the monitored mass in the SIM mode with the molecular weight (M-1) of IP3. The calibration curve was developed by injecting 50 μl of blank plasma samples spiked with a known amount of IP3. The retention time for IP3 was 2.62 min. FIG. 5 shows a typical chromatogram obtained with these samples.

Example 11

Determination of IP6 (Inositol Hexaphosphate) in Human, Rat and Dog Plasma and in Human and Rat Urine (MRM Mode)

The bioanalytical method developed in Example 1 and used in example 1-10 was transferred to the MRM mode in an UPLC®-MS/MS system. The use of this MRM mode resulted in an increase of the analytical sensitivity as well as selectivity improvement.

Figure 6:
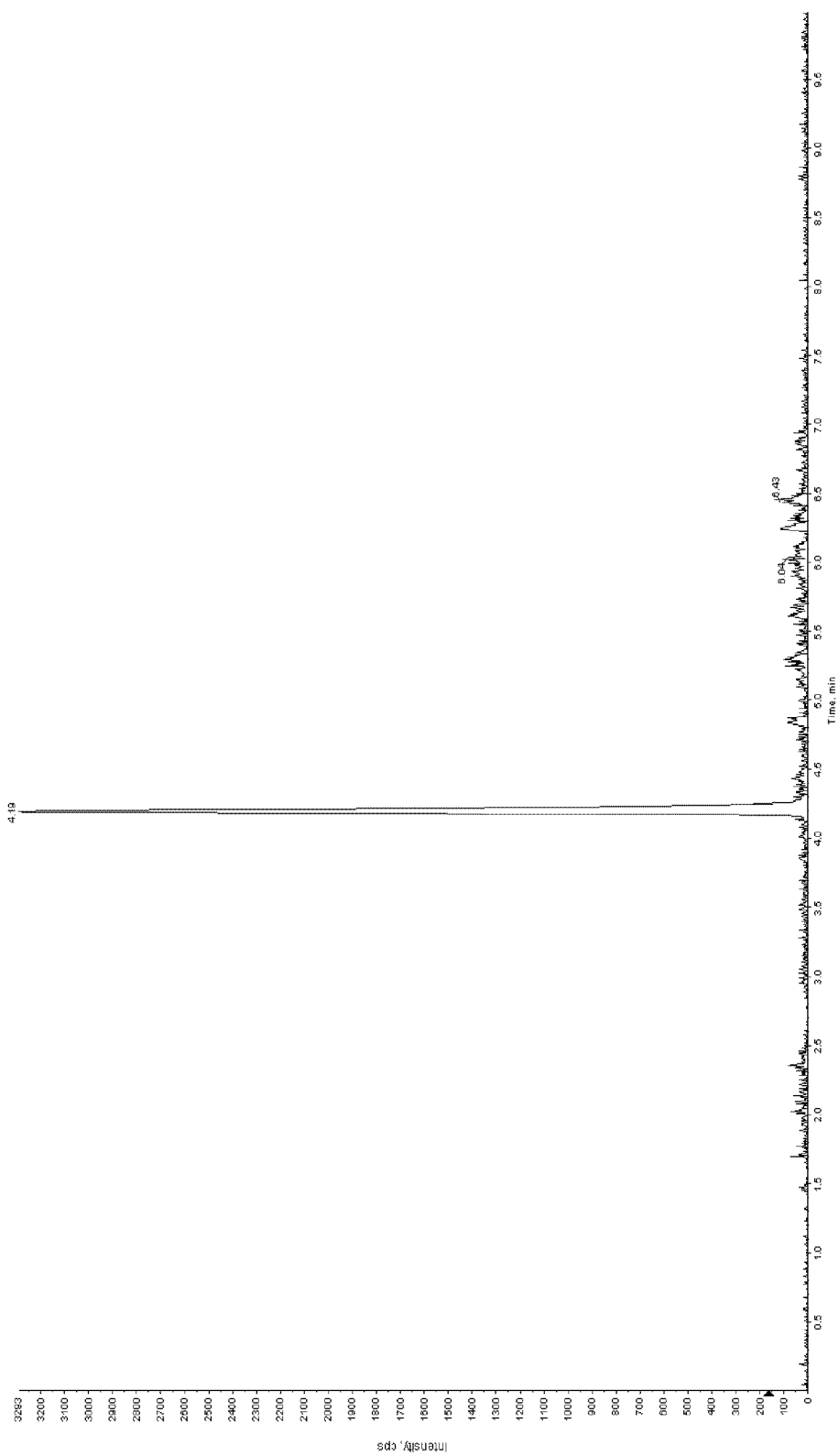
FIG. 6. Typical Chromatogram of IP6 in human urine (Example 11).

The same extraction procedure was used. Chromatographic conditions were also based on the same theory. The mass transition obtained after collision-induced dissociation and used for quantitative purpose of IP6 was m/z 659.0>m/z 560.9. FIG. 6 shows a typical chromatogram obtained with these samples.

Example 12

Determination of IP6 in a Surrogate Matrix (Serum or Plasma Surrogate Matrix)

Figure 7:
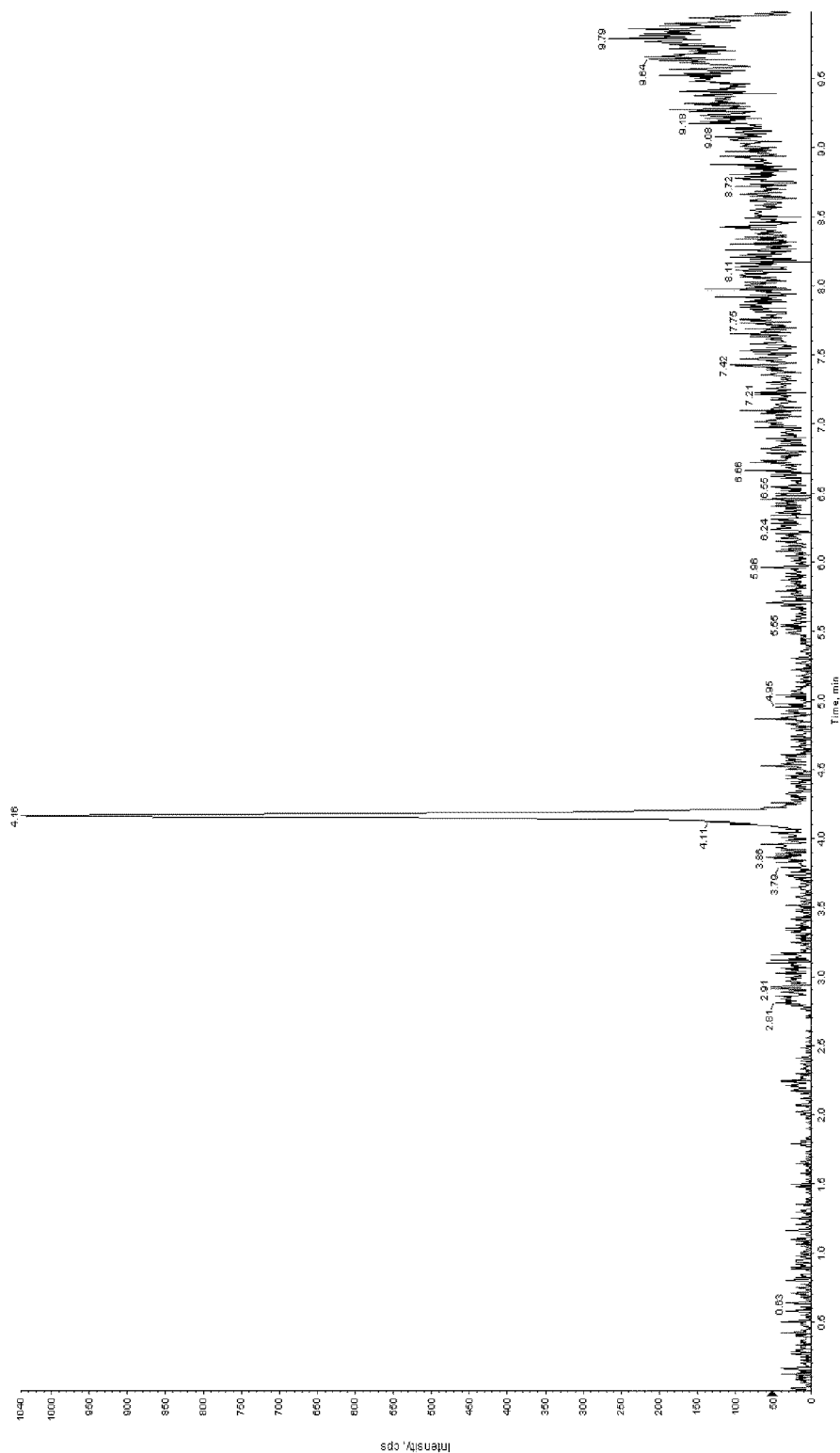
FIG. 7. Typical Chromatogram of IP6 using a solution of 30 mg BSA (Bovine Serum Albumin)/mL in PBS as a surrogate matrix for plasma or serum (Example 12).

The bioanalytical procedure developed in Example 11, was applied in a surrogate matrix. In a particular situation (e.g. constitutive levels of the analyte are expected in the blank matrix) a surrogate matrix could be used to prepare the calibration curve and to quantify IP6 in biological samples. A similar matrix effect as well as the same extraction recovery between surrogate matrix and biological matrix was observed resulting in an identical behavior in the UPLC®-MS/MS system. As a surrogate matrix for plasma or serum, a solution of 30 mg BSA (Bovine Serum Albumin)/mL in PBS was used. This modification gives a higher sensitivity and avoids the use of natural biological matrices to build the calibration curve. FIG. 7 shows a typical chromatogram obtained with these samples.

Example 13

Determination of IP6 and Related Impurities in Formulations (SCAN Mode)

The chromatographic method developed for the determination of Phytic Acid permitted to determine some impurities presents in a Phytic Acid solution, all the detected impurities (IP3, IP4, IP5 and m/z 779) coeluted with the peak of Phytic Acid; however, they were detected due to their different molecular weight. IP5 was the most abundant impurity.

Figure 8:
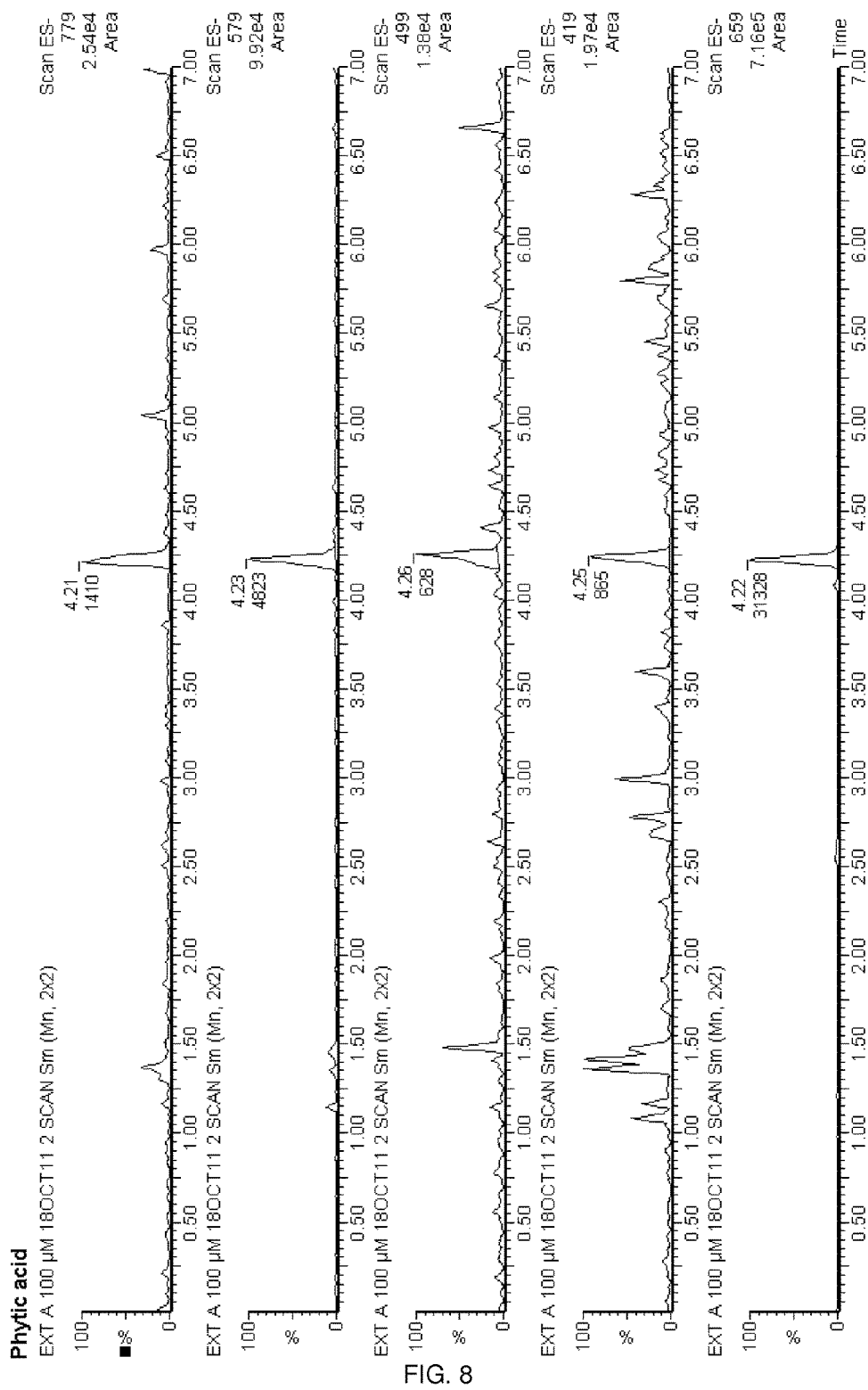
FIG. 8. Typical Chromatogram of the impurities present in a Phytic Acid solution: IP5, IP4, IP3 and m/z 779 (Example 13)

FIG. 8 shows a chromatogram obtained for this example.

Example 14

Determination of IP6 and Related Metabolites in Rat Hepatocytes (SCAN Mode)

Phytic Acid and its metabolites were detected after incubation of Phytic Acid in rat hepatocytes. The purification step involved a dilution of the pellets with KHB medium after precipitation with EDTA and finally a dilution with TEAA. Only IP1 and IP2 were eluted with significant differences in the retention time relative to Phytic Acid.

Figure 9:
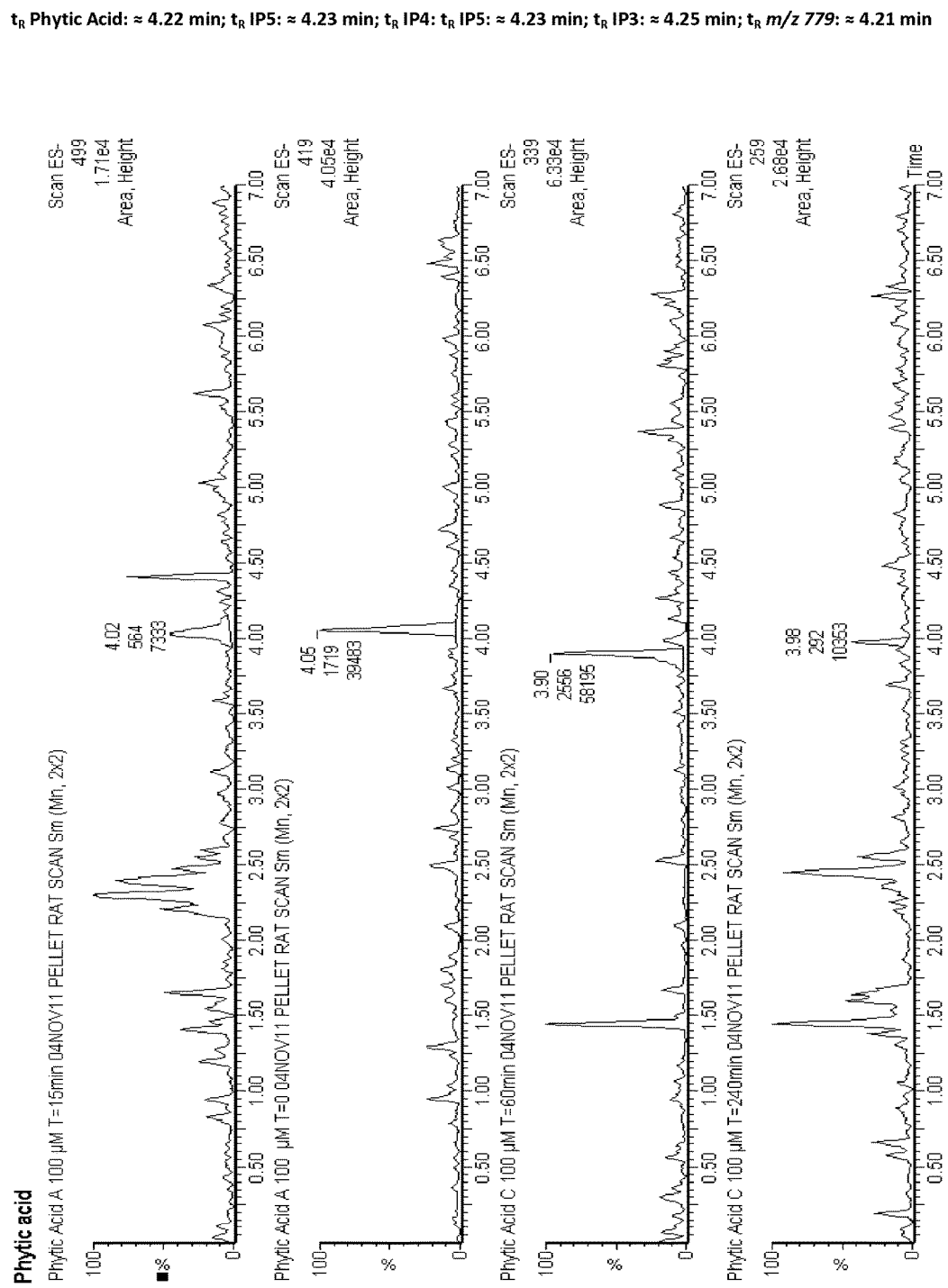
FIG. 9. Typical Chromatogram of Phytic Acid metabolites m/z 779, m/z 740 y m/z 579 after incubation of Phytic Acid in rat hepatocytes (Example 14)
Figure 10:
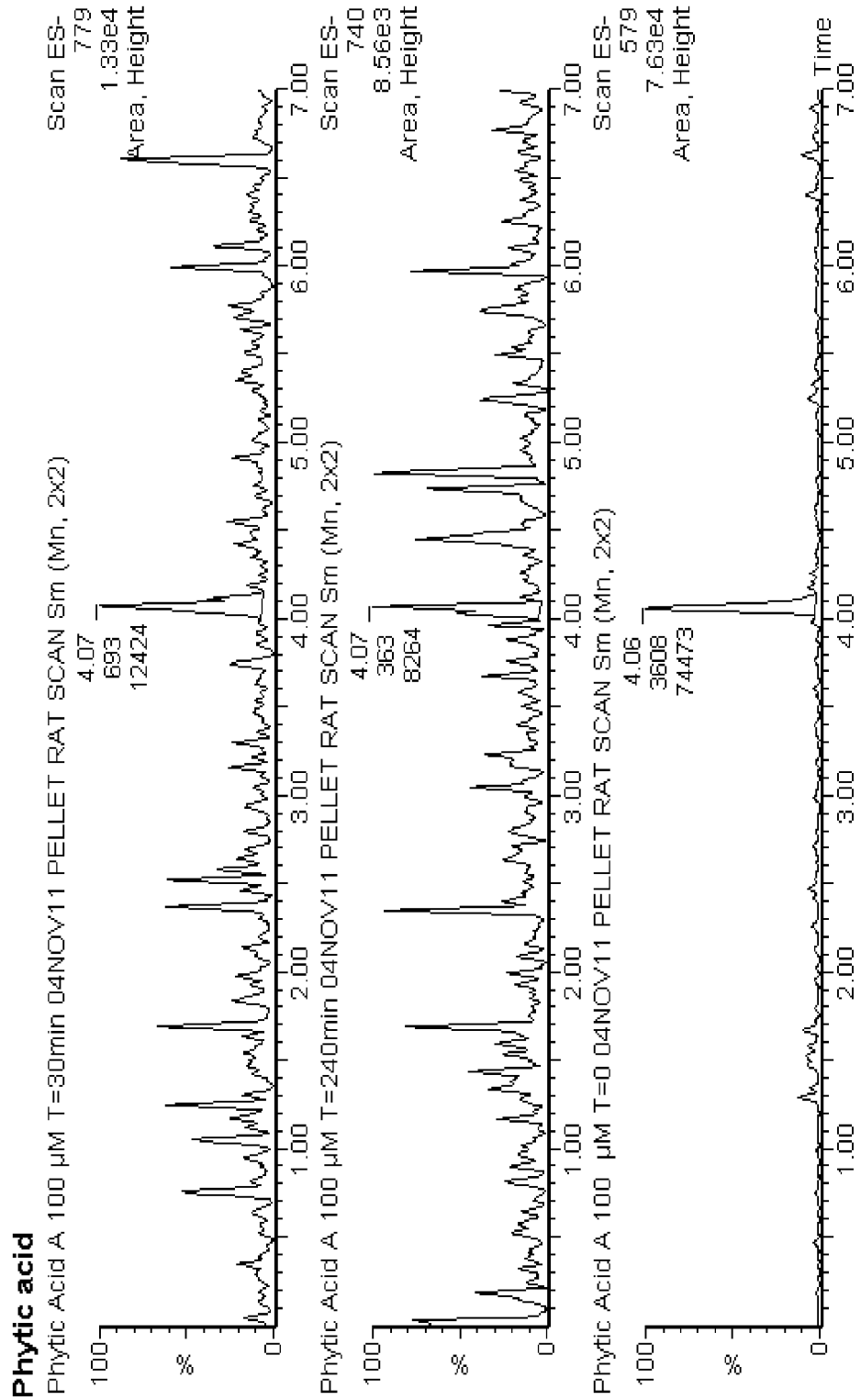
FIG. 10. Typical Chromatogram of Phytic Acid metabolites m/z 499, m/z 419, m/z 339 y m/z 259 after incubation of Phytic Acid in rat hepatocytes (Example 14)
Figure 11:
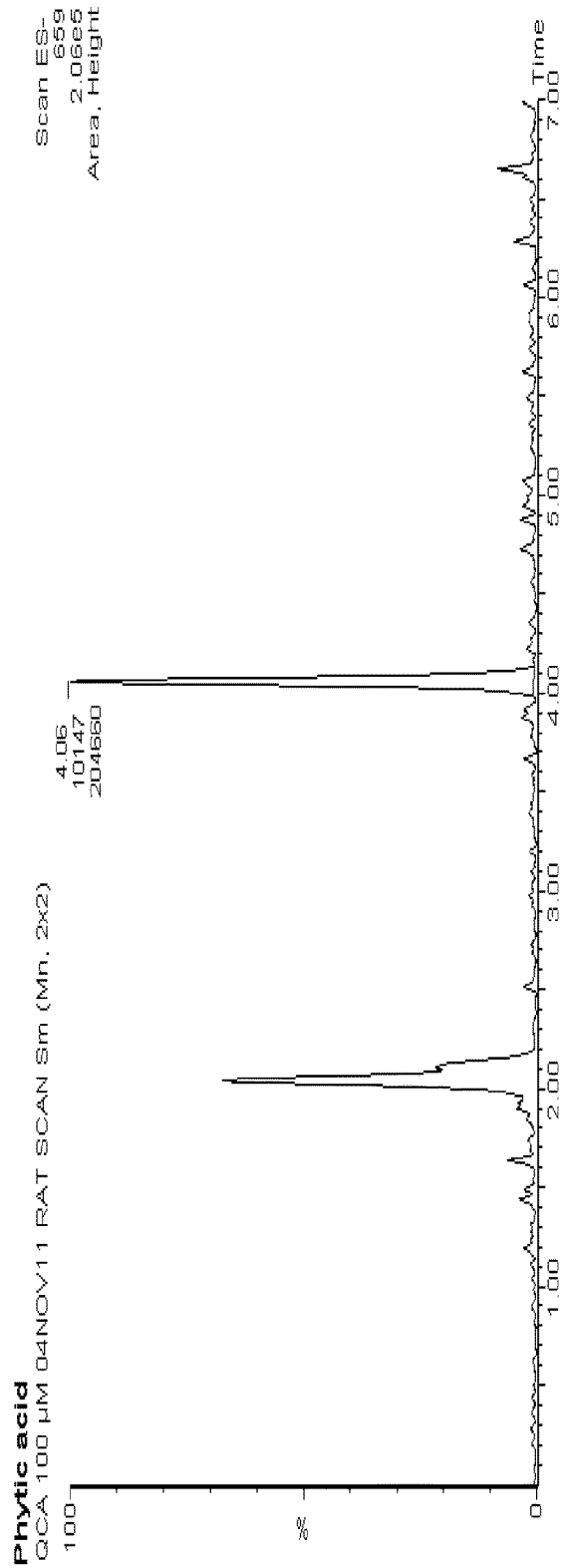
FIG. 11. Typical Chromatogram of Phytic Acid after incubation of Phytic Acid in rat hepatocytes (Example 14)

FIGS. 9, 10 and 11 show typical chromatograms of Phytic Acid and its metabolites after incubation of Phytic Acid in rat hepatocytes.

Example 15

Determination of IP5 in Dog and Rat Plasma Samples (SIM Mode)

The bioanalytical procedure developed in Example 1, was applied in the determination of IP5 in dog and rat plasma.

IP5 was detected in the SIM mode using molecular weight (M-1) of IP5. The retention time for IP5 was 4.10 min.

Figure 12:
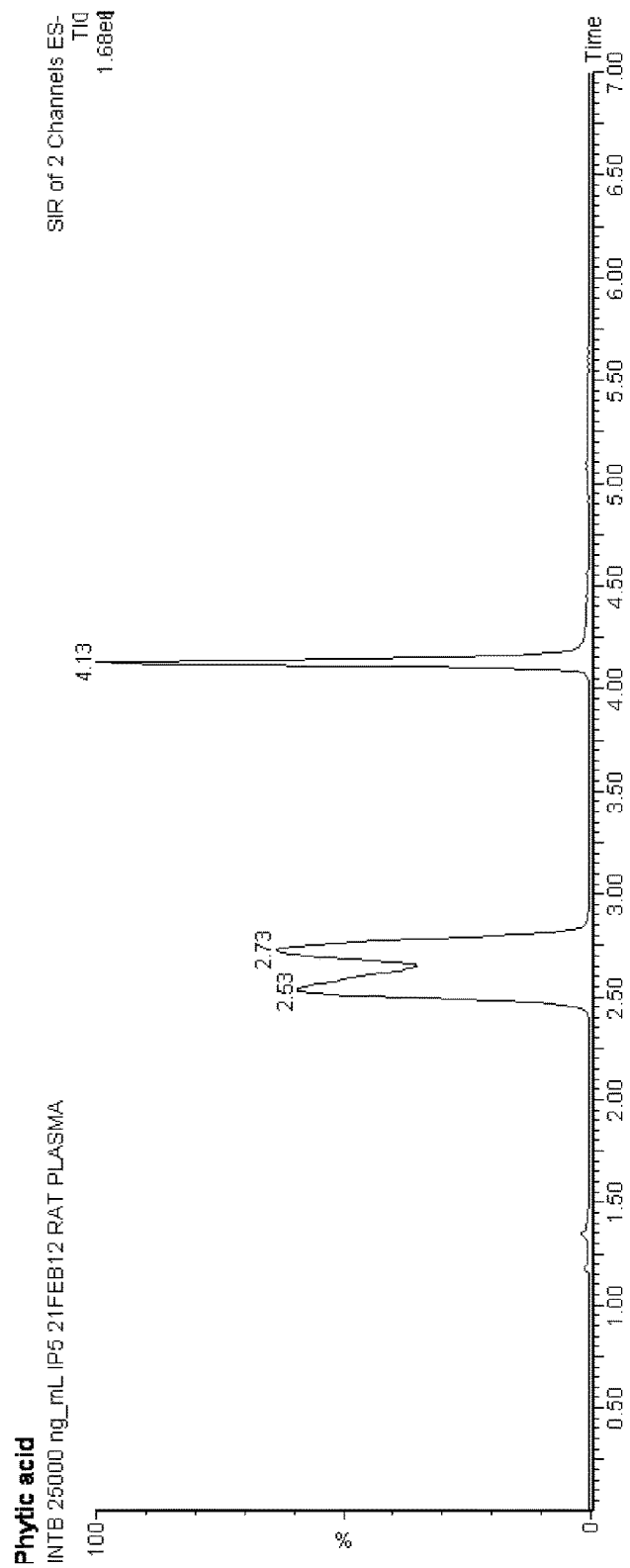
FIG. 12. Typical Chromatogram of IP5 in rat plasma (Example 15)

FIG. 12 shows a typical chromatogram obtained for IP5 in rat plasma.

Example 16

Determination of Phytic Acid Metabolites in Rat Plasma Samples (SIM Mode)

The bioanalytical procedure developed for the determination of Phytic Acid was applied to rat plasma samples in order to detect the maximum number of metabolites.

Figure 13:
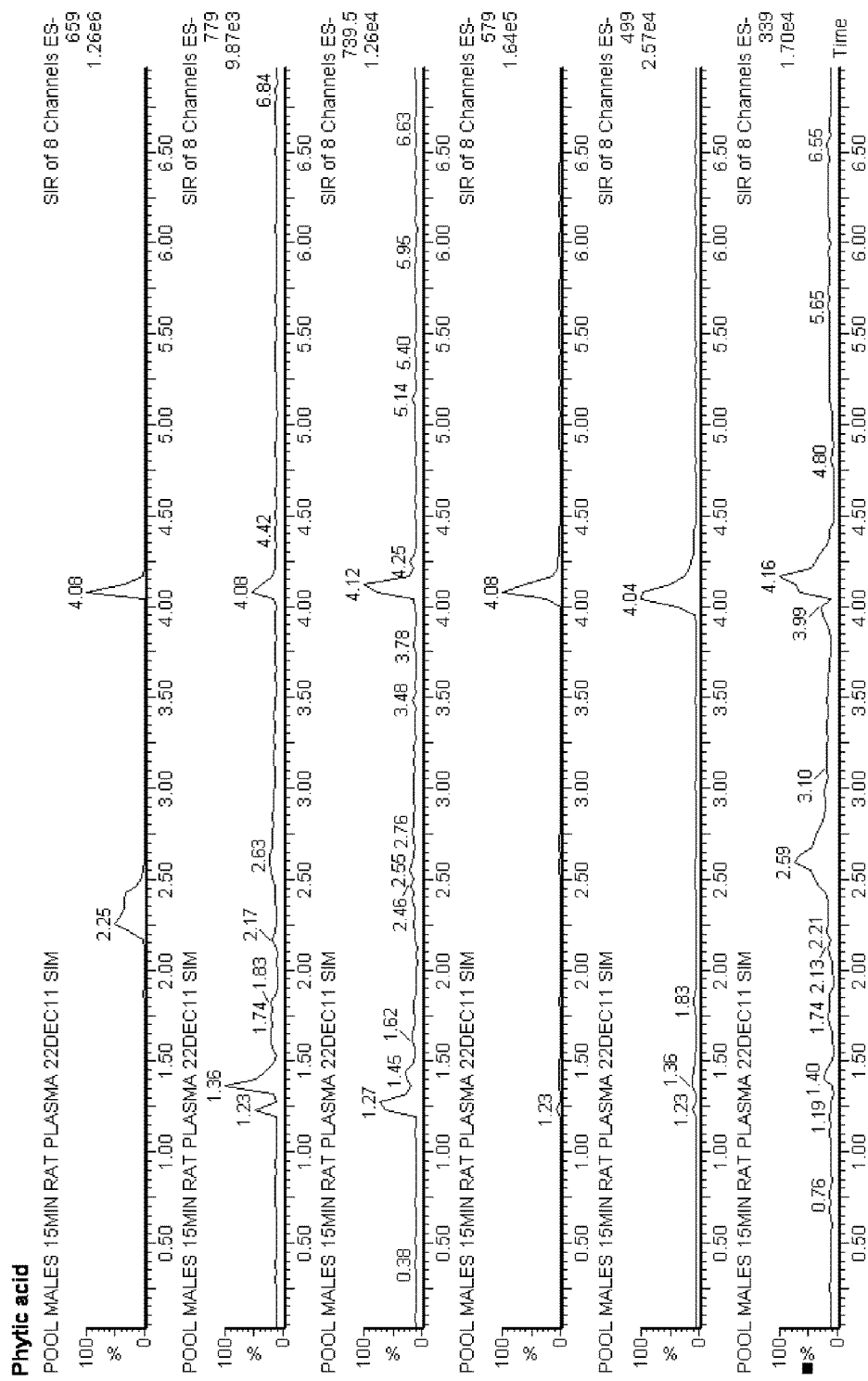
FIG. 13. Typical Chromatogram of Phytic Acid metabolites (metabolic profile) in rat plasma (Example 16)

The metabolites were firstly detected in the SCAN mode and then confirmed and semi-quantified by SIM mode. Quantitative measurements can be performed obtaining (i.e. synthesizing) the corresponding metabolites to prepare standards. FIG. 13 shows a typical chromatogram obtained with these samples.

Example 17

Determination of Metabolites of Phytic Acid in Dog Plasma Samples (SIM Mode)

The bioanalytical procedure developed for the determination of Phytic Acid was applied to dog plasma samples in order to detect the maximum number of metabolites. The metabolites were firstly detected in the SCAN mode and then confirmed and semi-quantified by SIM mode. Quantitative measurements can be performed obtaining (i.e. synthesizing) the corresponding metabolites to prepare standards.

Figure 14:
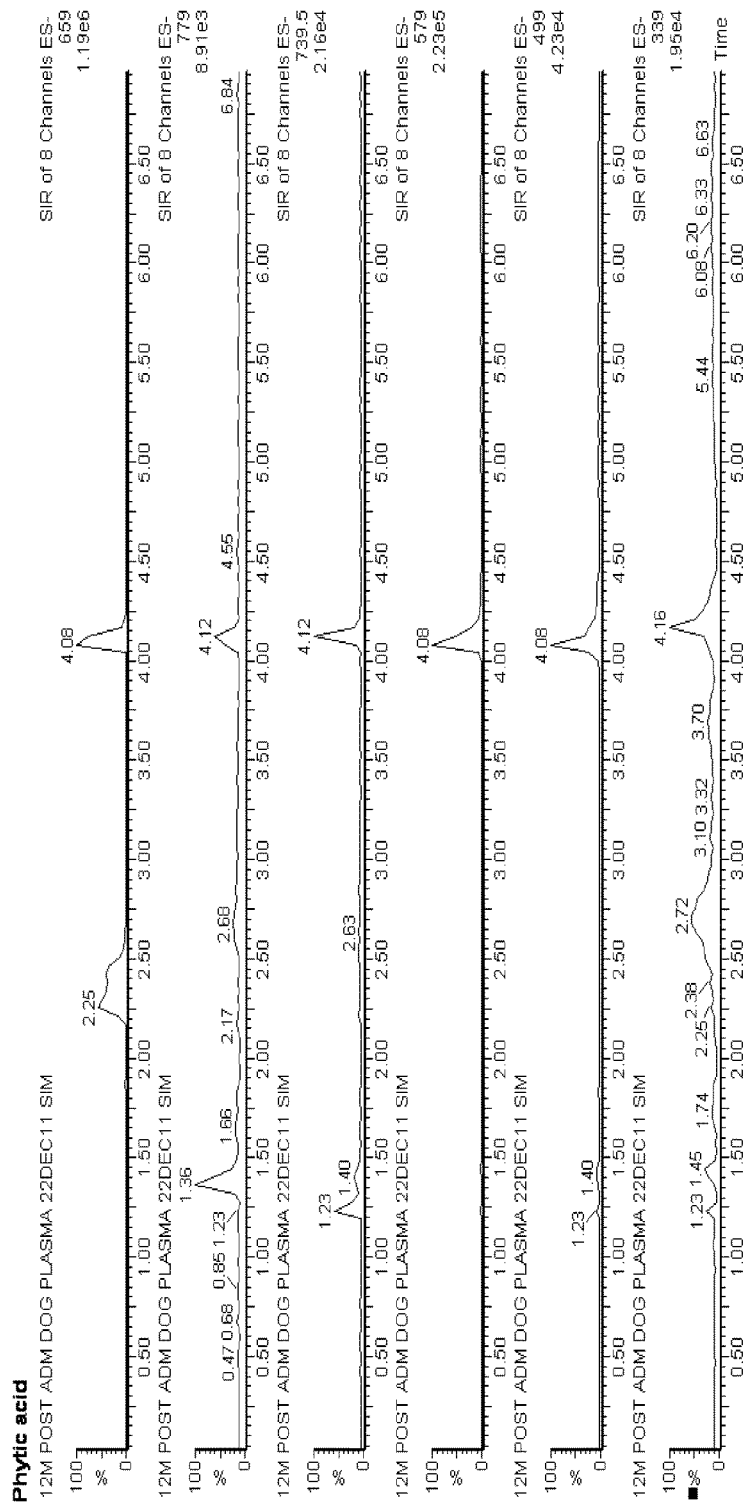
FIG. 14. Typical Chromatogram of Phytic Acid metabolites (metabolic profile) in dog plasma (Example 17)

FIG. 14 shows a typical chromatogram obtained with these samples.

Example 18

Determination of Phytic Acid (Identity, Assay) and Related Impurities in Formulations for Quality Control of an API, a Medical Food, a Reagent, a Food Additive, a Pharmaceutical Composition or Nutraceutical Phytic acid and related impurities have been identified and quantified in formulations in aqueous solution. This method allows the calculation of the assay and chromatographic purity of phytic acid.

The determination and quantification of phytic acid was carried out by Ion Chromatography with post column derivatization by UV detection.

The ion-chromatography column used was a polystyrene 2% cross-linked with divinylbenzene polymer. The flow rate was maintained at 1 mL/min, setting a column temperature of 35° C.

Adequate sensitivity for phytic acid related compounds was obtained by using post-column derivatization and UV detection.

Figure 15:
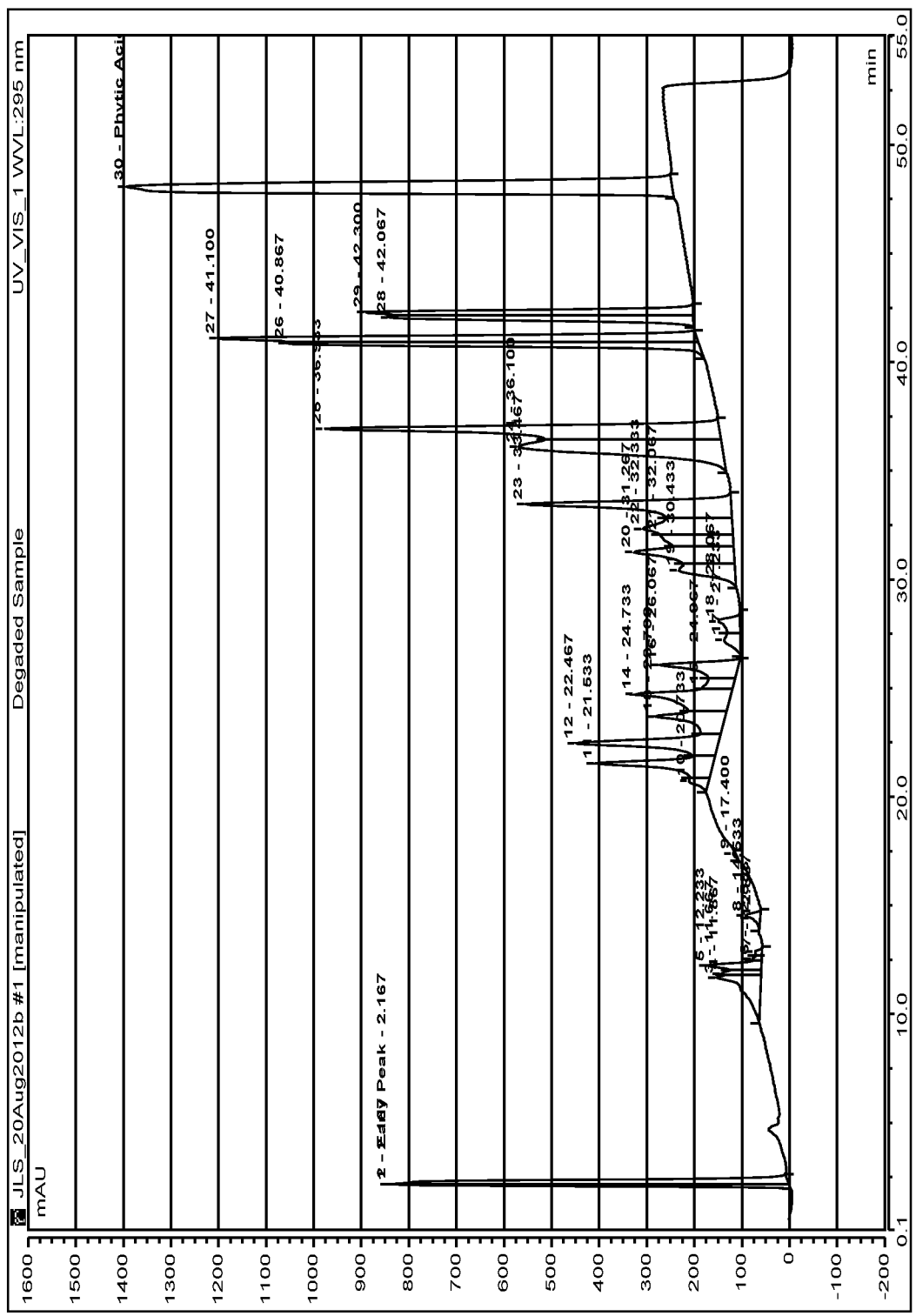
FIG. 15. Typical Chromatogram of an API sample, showing the corresponding peaks for Phytic Acid and its related impurities (impurities profile) (Example 18)

The retention time for phytic acid was 48.06 minutes (see FIG. 15). The identity of phytic is confirmed when the retention time of the main peak in the assay sample is within ±0.5 minutes of the mean retention time of the peak corresponding to phytic acid for all injections of the assay working standard.

This analytical technique allows the simultaneous determination of phytic acid together with its related impurities (up to thirty five) in a single chromatographic run for quality control of an API, a medical food, a reagent, a food additive, a pharmaceutical composition or nutraceutical.

Based upon tentative assignments from comparison of the relative retention times of the impurities formed with the literature method the major impurities formed are identified as listed in Table 1.

TABLE 1

Tentative impurity peak assignments for degraded sample

| Peak | Retention Time (min) | RRT |
|---|---|---|
| DL-Ins(1, 5, 6)P3 | 17.400 | 0.36 |
| — | 21.533 | 0.45 |
| — | 22.467 | 0.47 |
| DL-Ins(1, 2, 4, 6)P4 + Ins(1, 2, 3, 5)P4 | 23.709 | 0.49 |
| DL-Ins(1, 2, 3, 4)P4 + Ins(1, 3, 4, 6)P4 | 24.733 | 0.51 |
| DL-Ins(1, 2, 4, 5)P4 | 24.967 | 0.52 |
| DL-Ins(1, 2, 4, 5)P4 | 27.233 | 0.57 |
| DL-Ins(1, 2, 5, 6)P4 | 28.067 | 0.58 |
| Ins(2, 4, 5, 6)P4 | 30.433 | 0.63 |
|  | 31.267 | 0.65 |
|  | 32.067 | 0.67 |
|  | 32.333 | 0.67 |
| DL-Ins(1, 4, 5, 6)P4 | 33.467 | 0.70 |
| Ins(1, 2, 3, 4, 6)P5 | 36.100 | 0.75 |
| DL-Ins(1, 2, 3, 4, 5)P5 | 36.933 | 0.77 |
| DL-Ins(1, 2, 4, 5, 6)P5 | 40.867 | 0.85 |
|  | 41.100 | 0.86 |
| Ins(1, 3, 4, 5, 6)P5 | 42.067 | 0.88 |
|  | 42.300 | 0.88 |
| Phytic Acid | 48.067 | 1.00 |

The invention claimed is:

1. A method for the direct identification and quantification of at least one phosphorus containing compound having a molecular weight of at least 200 daltons in a biological sample
   wherein said biological sample is obtained from a biological fluid selected from the group consisting of blood, plasma, serum, urine, saliva, lymphatic liquid, cerebrospinal fluid and combinations thereof, wherein said biological fluid has been treated with a precipitating agent, a chelating agent, or a combination thereof,
   wherein said at least one phosphorus containing compound to be identified and quantified in the biological sample is selected from:
      (a) a bisphosphonate or polyphosphonate;
      (b) a hexametaphosphate;
      (c) a C3-C7 cycloalkyl substituted compound with at least two —R groups wherein each —R group is —OH, —OP(O)(OH)$_2$ or —P(O)(OH)$_2$, and wherein at least two —R groups are independently selected from —P(O)(OH)$_2$ and —OP(O)(OH)$_2$ and said C3-C7 cycloalkyl is cyclopropyl, cyclobutyl, cyclopentyl, cyclohexyl, or cyclohelptyl;
      (d) ions or salts thereof; or,
      (e) a combination thereof,
   said method comprising:
      (i) preparing at least one standard sample of a phosphorus containing compound to be identified and quantified;
      (ii) preparing a biological sample containing the at least one phosphorus containing compound to be identified and quantified, wherein the process to prepare said biological sample comprises at least partially or totally dissolving said biological sample to form a solution or a slurry containing the compound;
      (iii) introducing the at least one standard sample together or sequentially with the biological sample into a stream of a solvent system, wherein the solvent system is a polar solvent or a solvent mixture comprising at least one polar solvent and passing the samples through at least one chromatography column containing small particles of resin wherein the column is essentially filled of the small particles in a stationary phase while maintaining the pressure of the system in the chromatography column between 5 and 1500 atm;

(iv) identifying the retention time and/or quantifying the intensity of the signal of the at least one phosphorus containing compound to be identified and quantified by means of a mass spectrometry detector when the samples are eluted from the chromatography column;

wherein in said direct identification and quantification of the at least one phosphorus containing compound in said biological sample is not radiolabeled or derivatized.

2. The method according to claim 1, wherein the C3-C7 cycloalkyl substituted compound is an inositol polyphosphate comprising from 2 to 6 phosphate groups.

3. The method according to claim 2, wherein the inositol polyphosphate is phytate.

4. The method according to claim 1, wherein the biological fluid is an isolated sample obtained from a human subject who is under a bioequivalence study.

5. The method according to claim 1, wherein the method is used to identify and quantify any metabolites of the at least one phosphorus containing compound in a metabolic profile.

6. The method according to claim 1, wherein the pH of the solvent system is between 7 and 14.

7. The method according to claim 1, wherein the mass spectrometry detector is a tandem mass spectrometer, a triple quadrupole spectrometer, or a single quadrupole spectrometer.

8. The method according to claim 1, wherein the mass spectrometry detector operates under selected ion monitoring (SIM) mode, multiple reaction monitoring (MRM) mode, selected reaction monitoring (SRM) mode, SCAN (positive/negative), or a combination thereof.

9. The method according to claim 1, wherein the standard sample is a reference standard, an external standard, an internal standard, or an standard addition.

* * * * *